United States Patent
Bowers et al.

(10) Patent No.: US 8,047,714 B2
(45) Date of Patent: Nov. 1, 2011

(54) DIAGNOSTIC DELIVERY SERVICE

(75) Inventors: Jeffrey A. Bowers, Kirkland, WA (US);
Roderick A. Hyde, Redmond, WA (US);
Muriel Y. Ishikawa, Livermore, CA (US); Jordin T. Kare, Seattle, WA (US);
Eric C. Leuthardt, St. Louis, MO (US);
Dennis J. Rivet, Portsmouth, VA (US);
Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 182 days.

(21) Appl. No.: 12/322,330

(22) Filed: Jan. 29, 2009

(65) Prior Publication Data

US 2010/0191091 A1 Jul. 29, 2010

Related U.S. Application Data

(63) Continuation-in-part of application No. 12/322,326, filed on Jan. 29, 2009, and a continuation-in-part of application No. 12/322,331, filed on Jan. 29, 2009, and a continuation-in-part of application No. 12/322,358, filed on Jan. 29, 2009, and a continuation-in-part of application No. 12/322,333, filed on Jan. 29, 2009, and a continuation-in-part of application No. 12/322,353, filed on Jan. 29, 2009, and a continuation-in-part of application No. 12/322,357, filed on Jan. 29, 2009, and a continuation-in-part of application No. 12/322,334, filed on Jan. 29, 2009, and a continuation-in-part of application No. 12/322,327, filed on Jan. 29, 2009.

(51) Int. Cl.
*H05G 1/64* (2006.01)
*H05G 1/08* (2006.01)
(52) U.S. Cl. ......... 378/189; 378/102; 378/182; 378/192
(58) Field of Classification Search .................. 378/182, 378/184, 189–192, 102
See application file for complete search history.

(56) References Cited

U.S. PATENT DOCUMENTS

| | | | |
|---|---|---|---|
| 2,290,767 A * | 7/1942 | Reuter | .......................... 378/190 |
| 4,207,470 A | 6/1980 | Heisner et al. | |
| 4,534,051 A | 8/1985 | Grady et al. | |
| 4,798,446 A | 1/1989 | Hettrick | |
| 4,991,193 A | 2/1991 | Cecil et al. | |
| 5,090,038 A | 2/1992 | Asahina | |
| 5,091,926 A | 2/1992 | Horton et al. | |
| 5,177,778 A | 1/1993 | Tsurumaki et al. | |
| 5,206,894 A | 4/1993 | Makrinos et al. | |
| 5,474,064 A | 12/1995 | Rohrberg | |

(Continued)

OTHER PUBLICATIONS

Leng, Shuai et al.; "Helical Cone-Beam Computed Tomography Image Reconstruction Algorithm for a Tilted Gantry with N-P1 Data Acquisition"; Optical Engineering; dated Jan. 2007; pp. 015004.1-015004.14; vol. 46, No. 1; SPIE.

*Primary Examiner* — Edward Glick
*Assistant Examiner* — Thomas R Artman

(57) ABSTRACT

Systems, methods, and other modalities are described for (a) obtaining an indication relating to an emission module (which may be dangerous, e.g.) or its user (who may be untrained, e.g.) and for (b) configuring the module or causing an irradiation (for imaging, e.g.) in response to the indication.

43 Claims, 19 Drawing Sheets

U.S. PATENT DOCUMENTS

| | | | |
|---|---|---|---|
| 5,524,624 A | 6/1996 | Tepper et al. | |
| 5,533,087 A | 7/1996 | Snoeren | |
| 5,550,380 A | 8/1996 | Sugawara et al. | |
| 5,572,995 A | 11/1996 | Rohrberg | |
| 5,583,343 A * | 12/1996 | Dilmanian et al. | 250/475.2 |
| 5,590,767 A | 1/1997 | Li | |
| 5,606,165 A | 2/1997 | Chiou et al. | |
| 5,631,943 A * | 5/1997 | Miles | 378/102 |
| 5,669,708 A | 9/1997 | Mashima et al. | |
| 5,769,790 A | 6/1998 | Watkins et al. | |
| 5,812,631 A | 9/1998 | Yan et al. | |
| 5,822,737 A | 10/1998 | Ogram | |
| 5,841,397 A | 11/1998 | Hopkins | |
| 5,894,844 A | 4/1999 | Rohrberg | |
| 5,944,684 A | 8/1999 | Roberts et al. | |
| 5,963,917 A | 10/1999 | Ogram | |
| 5,979,457 A | 11/1999 | Rohrberg | |
| 6,065,154 A | 5/2000 | Hulings et al. | |
| 6,066,243 A | 5/2000 | Anderson et al. | |
| 6,081,676 A | 6/2000 | Inomata | |
| 6,094,472 A | 7/2000 | Smith | |
| 6,094,589 A * | 7/2000 | Schmitt | 600/407 |
| 6,097,112 A | 8/2000 | Kondo | |
| 6,097,344 A | 8/2000 | Anderson | |
| 6,112,502 A | 9/2000 | Frederick et al. | |
| 6,122,396 A | 9/2000 | King et al. | |
| 6,134,460 A | 10/2000 | Chance | |
| 6,139,499 A | 10/2000 | Wilk | |
| 6,192,105 B1 | 2/2001 | Hunter et al. | |
| 6,195,579 B1 | 2/2001 | Carroll et al. | |
| 6,234,969 B1 | 5/2001 | Chaintreuil et al. | |
| 6,241,683 B1 | 6/2001 | Macklem et al. | |
| 6,246,463 B1 | 6/2001 | Hamada et al. | |
| 6,259,358 B1 | 7/2001 | Fjordbotten | |
| 6,261,293 B1 | 7/2001 | Nicholson et al. | |
| 6,278,490 B1 | 8/2001 | Fukuda et al. | |
| 6,296,896 B1 | 10/2001 | Takahashi et al. | |
| 6,320,938 B1 | 11/2001 | Hopper | |
| 6,346,880 B1 | 2/2002 | Schroeder et al. | |
| 6,359,651 B1 | 3/2002 | Yokonuma | |
| 6,359,961 B1 | 3/2002 | Aufrichtig et al. | |
| 6,366,737 B1 | 4/2002 | Numako et al. | |
| 6,373,916 B1 | 4/2002 | Inoue et al. | |
| 6,380,958 B1 | 4/2002 | Guendel et al. | |
| 6,383,135 B1 | 5/2002 | Chikovani et al. | |
| 6,400,741 B1 | 6/2002 | Matsunaga et al. | |
| 6,423,963 B1 | 7/2002 | Wu | |
| 6,429,431 B1 * | 8/2002 | Wilk | 250/363.02 |
| 6,449,337 B1 | 9/2002 | Honda et al. | |
| 6,449,340 B1 | 9/2002 | Tybinkowski et al. | |
| 6,459,767 B1 | 10/2002 | Boyer | |
| 6,460,093 B1 | 10/2002 | Taugher | |
| 6,467,905 B1 | 10/2002 | Stahl et al. | |
| 6,478,739 B1 | 11/2002 | Hong | |
| 6,478,740 B2 | 11/2002 | Souney et al. | |
| 6,479,981 B2 | 11/2002 | Schweitzer, Jr. et al. | |
| 6,487,804 B1 | 12/2002 | Petrella, Jr. | |
| 6,496,957 B1 | 12/2002 | Kumagai | |
| 6,507,638 B2 | 1/2003 | Curtis et al. | |
| 6,507,699 B2 | 1/2003 | Lemoine | |
| 6,529,280 B1 | 3/2003 | Yahashi et al. | |
| 6,540,685 B1 | 4/2003 | Rhoads et al. | |
| 6,546,276 B1 | 4/2003 | Zanelli | |
| 6,549,609 B1 | 4/2003 | Iinuma et al. | |
| 6,553,245 B1 | 4/2003 | Grace et al. | |
| 6,556,696 B1 | 4/2003 | Summers et al. | |
| 6,569,157 B1 | 5/2003 | Shain et al. | |
| 6,583,420 B1 | 6/2003 | Nelson et al. | |
| 6,584,587 B1 | 6/2003 | McDermott | |
| 6,585,652 B2 | 7/2003 | Lang et al. | |
| 6,585,684 B1 | 7/2003 | Hughett et al. | |
| 6,588,432 B1 | 7/2003 | Rehder et al. | |
| 6,594,634 B1 | 7/2003 | Hampton et al. | |
| 6,597,291 B2 | 7/2003 | Tsui | |
| 6,612,982 B1 | 9/2003 | Ouchi | |
| 6,616,671 B2 | 9/2003 | Landry et al. | |
| 6,617,963 B1 | 9/2003 | Watters et al. | |
| 6,618,465 B2 | 9/2003 | Mohr et al. | |
| 6,652,461 B1 | 11/2003 | Levkovitz | |
| 6,658,597 B1 | 12/2003 | Ker et al. | |
| 6,660,022 B1 | 12/2003 | Li et al. | |
| 6,662,792 B2 | 12/2003 | Dutt et al. | |
| 6,668,040 B2 | 12/2003 | Cederstrom | |
| 6,671,541 B2 | 12/2003 | Bishop et al. | |
| 6,681,771 B2 | 1/2004 | Durette | |
| 6,687,331 B1 | 2/2004 | Muller et al. | |
| 6,690,958 B1 | 2/2004 | Walker et al. | |
| 6,737,247 B2 | 5/2004 | Bogdanov et al. | |
| 6,745,071 B1 | 6/2004 | Anderson et al. | |
| 6,751,688 B1 | 6/2004 | El-Demerdash et al. | |
| 6,753,533 B2 | 6/2004 | Mita | |
| 6,768,425 B2 | 7/2004 | Flaherty et al. | |
| 6,768,925 B2 | 7/2004 | Fenn et al. | |
| 6,775,352 B2 | 8/2004 | Toth et al. | |
| 6,779,920 B2 | 8/2004 | Stevanovic et al. | |
| 6,787,937 B2 | 9/2004 | Mody et al. | |
| 6,789,900 B2 | 9/2004 | Van de Velde | |
| 6,802,753 B1 | 10/2004 | Ando et al. | |
| 6,816,564 B2 | 11/2004 | Charles, Jr. et al. | |
| 6,825,454 B2 | 11/2004 | Czarnetzki et al. | |
| 6,826,365 B1 | 11/2004 | Constable | |
| 6,830,549 B2 | 12/2004 | Bui et al. | |
| 6,830,568 B1 | 12/2004 | Kesten et al. | |
| 6,831,664 B2 | 12/2004 | Marmaropoulos et al. | |
| 6,844,150 B2 | 1/2005 | Weiss et al. | |
| 6,864,478 B2 | 3/2005 | Schroder | |
| 6,865,254 B2 | 3/2005 | Näfstadius | |
| 6,869,427 B1 | 3/2005 | Shokoohi | |
| 6,870,521 B2 | 3/2005 | Iwami | |
| 6,873,569 B2 | 3/2005 | Vernet et al. | |
| 6,885,885 B1 | 4/2005 | Takizawa et al. | |
| 6,892,096 B2 | 5/2005 | Lyden | |
| 6,909,774 B2 | 6/2005 | Oshino et al. | |
| 6,910,999 B2 | 6/2005 | Chin et al. | |
| 6,932,807 B1 | 8/2005 | Tomita et al. | |
| 6,932,818 B2 | 8/2005 | Behrens | |
| 6,939,319 B1 | 9/2005 | Anstead et al. | |
| 6,947,522 B2 | 9/2005 | Wilson et al. | |
| 6,948,995 B2 | 9/2005 | Ishikura et al. | |
| 6,954,918 B2 | 10/2005 | Houston | |
| 6,965,118 B2 | 11/2005 | Martin et al. | |
| 6,971,991 B2 | 12/2005 | Lasser et al. | |
| 6,975,894 B2 | 12/2005 | Wehrli et al. | |
| 6,977,375 B2 | 12/2005 | Yin et al. | |
| 6,981,147 B1 | 12/2005 | Hamann et al. | |
| 6,984,051 B2 | 1/2006 | Takino | |
| 6,998,005 B2 | 2/2006 | Magee et al. | |
| 7,000,827 B2 | 2/2006 | Meder | |
| 7,005,997 B1 | 2/2006 | Wiewiura | |
| 7,020,508 B2 | 3/2006 | Stivoric et al. | |
| 7,027,007 B2 | 4/2006 | Hossein | |
| 7,028,180 B1 | 4/2006 | Aull et al. | |
| 7,034,740 B2 | 4/2006 | Witten | |
| 7,035,374 B2 | 4/2006 | Chen | |
| 7,044,983 B1 | 5/2006 | Cheng | |
| 7,047,452 B2 | 5/2006 | Sessa et al. | |
| 7,052,458 B2 | 5/2006 | Pronk et al. | |
| 7,059,516 B2 | 6/2006 | Matsuyama et al. | |
| 7,068,226 B1 | 6/2006 | Mitra | |
| 7,068,752 B2 | 6/2006 | Brandt | |
| 7,071,692 B2 | 7/2006 | Branch et al. | |
| 7,076,436 B1 | 7/2006 | Ross, Jr. et al. | |
| 7,085,805 B1 | 8/2006 | Ruberg et al. | |
| 7,088,901 B2 | 8/2006 | Kim et al. | |
| 7,098,860 B2 | 8/2006 | Kaluzni et al. | |
| 7,102,123 B2 | 9/2006 | Chin et al. | |
| 7,102,580 B2 | 9/2006 | Matz et al. | |
| 7,104,649 B2 | 9/2006 | Otten, III et al. | |
| 7,105,828 B2 | 9/2006 | Unger et al. | |
| 7,108,663 B2 | 9/2006 | Talish et al. | |
| 7,109,505 B1 | 9/2006 | Sliski et al. | |
| 7,110,755 B2 | 9/2006 | Shibasaki et al. | |
| 7,114,676 B2 | 10/2006 | Elliott et al. | |
| 7,116,471 B2 | 10/2006 | Ghera et al. | |
| 7,116,749 B2 | 10/2006 | Besson | |
| 7,119,502 B2 | 10/2006 | Maishima | |
| 7,125,387 B2 | 10/2006 | Kawabata et al. | |

| Patent No. | Kind | Date | Inventor |
|---|---|---|---|
| 7,126,699 | B1 | 10/2006 | Wihl et al. |
| 7,137,712 | B2 | 11/2006 | Brunner et al. |
| 7,141,020 | B2 | 11/2006 | Poland et al. |
| 7,147,372 | B2 * | 12/2006 | Nelson et al. .................. 378/207 |
| 7,154,989 | B2 | 12/2006 | Ueno et al. |
| 7,154,991 | B2 | 12/2006 | Earnst et al. |
| 7,155,306 | B2 | 12/2006 | Haitin et al. |
| 7,156,709 | B1 | 1/2007 | Staerzl et al. |
| 7,156,879 | B1 | 1/2007 | Albrektsson et al. |
| 7,158,269 | B2 | 1/2007 | Morita |
| 7,170,968 | B2 | 1/2007 | Sukovic |
| 7,171,568 | B2 | 1/2007 | Dayan et al. |
| 7,172,564 | B2 | 2/2007 | Bosco |
| 7,173,571 | B2 | 2/2007 | Webb et al. |
| 7,178,688 | B2 | 2/2007 | Naufel et al. |
| 7,179,219 | B2 | 2/2007 | Matlock |
| 7,180,075 | B2 | 2/2007 | Brabec et al. |
| 7,180,470 | B1 | 2/2007 | Hentosh |
| 7,180,624 | B2 | 2/2007 | Tipirneni |
| 7,181,762 | B2 | 2/2007 | Jerdonek |
| 7,182,770 | B2 | 2/2007 | Falahee |
| 7,184,518 | B2 | 2/2007 | Chmeissani et al. |
| 7,185,656 | B2 | 3/2007 | Wakhloo et al. |
| 7,188,564 | B2 | 3/2007 | Ashikagaya |
| 7,188,625 | B2 | 3/2007 | Durette |
| 7,190,109 | B2 | 3/2007 | Lundahl et al. |
| 7,191,941 | B1 | 3/2007 | Mollett et al. |
| 7,194,298 | B2 | 3/2007 | Massicotte et al. |
| 7,197,107 | B2 | 3/2007 | Arai et al. |
| 7,203,539 | B2 | 4/2007 | Ware et al. |
| 7,206,375 | B2 | 4/2007 | Chen et al. |
| 7,207,963 | B2 | 4/2007 | Kania et al. |
| 7,211,814 | B2 | 5/2007 | Cadwalader et al. |
| 7,217,324 | B2 | 5/2007 | Bourgoin |
| 7,218,704 | B1 | 5/2007 | Adams et al. |
| 7,220,256 | B2 | 5/2007 | Hobart et al. |
| 7,224,218 | B1 | 5/2007 | Jiang et al. |
| 7,224,769 | B2 * | 5/2007 | Turner .......................... 378/98.2 |
| 7,226,208 | B2 | 6/2007 | Schmulenson |
| 7,233,645 | B2 | 6/2007 | Feda |
| 7,236,243 | B2 | 6/2007 | Beecroft et al. |
| 7,236,936 | B2 | 6/2007 | White et al. |
| 7,238,180 | B2 | 7/2007 | Mester et al. |
| 7,239,064 | B1 | 7/2007 | Jenkins et al. |
| 7,241,296 | B2 | 7/2007 | Buysse et al. |
| 7,242,817 | B2 | 7/2007 | Takeda et al. |
| 7,251,499 | B2 | 7/2007 | Ella et al. |
| 7,256,446 | B2 | 8/2007 | Hu et al. |
| 7,263,156 | B2 | 8/2007 | Roberts et al. |
| 7,266,407 | B2 | 9/2007 | Li et al. |
| 7,266,988 | B2 | 9/2007 | Kranz et al. |
| 7,272,251 | B2 | 9/2007 | Acar et al. |
| 7,274,766 | B2 | 9/2007 | Kaipio et al. |
| 7,276,681 | B2 | 10/2007 | Alexander et al. |
| 7,276,705 | B2 | 10/2007 | Leppert |
| 7,285,090 | B2 | 10/2007 | Stivoric et al. |
| 7,286,640 | B2 | 10/2007 | Yun et al. |
| 7,289,599 | B2 | 10/2007 | Seppi et al. |
| 7,289,603 | B2 | 10/2007 | Andrews et al. |
| 7,291,497 | B2 | 11/2007 | Holmes et al. |
| 7,291,841 | B2 | 11/2007 | Nelson et al. |
| 7,297,148 | B2 | 11/2007 | Waxman |
| 7,301,868 | B2 | 11/2007 | Mukaida |
| 7,303,555 | B2 | 12/2007 | Makin et al. |
| 7,304,605 | B2 | 12/2007 | Wells |
| 7,306,422 | B2 | 12/2007 | Dupuy et al. |
| 7,312,872 | B2 | 12/2007 | Ohta |
| 7,313,427 | B2 | 12/2007 | Benni |
| 7,313,840 | B2 | 1/2008 | Watkins |
| 7,315,607 | B2 | 1/2008 | Ramsauer |
| 7,317,821 | B2 | 1/2008 | Chen et al. |
| 7,318,550 | B2 | 1/2008 | Bonalle et al. |
| 7,320,319 | B2 | 1/2008 | Bonutti |
| 7,320,518 | B2 | 1/2008 | Miwa |
| 7,321,348 | B2 | 1/2008 | Cok et al. |
| 7,322,951 | B2 | 1/2008 | Reinhardt |
| 7,324,842 | B2 | 1/2008 | Dale et al. |
| 7,324,843 | B2 | 1/2008 | Pronk |
| 7,327,452 | B2 | 2/2008 | Frank et al. |
| 7,328,060 | B2 | 2/2008 | Mooradian et al. |
| 7,330,531 | B1 | 2/2008 | Karellas |
| 7,335,899 | B2 | 2/2008 | Blanton et al. |
| 7,336,018 | B2 | 2/2008 | Augesky |
| 7,336,763 | B2 | 2/2008 | Spartiotis et al. |
| 7,339,603 | B2 | 3/2008 | Ishizawa et al. |
| 7,342,368 | B2 | 3/2008 | Roman |
| 7,342,398 | B2 | 3/2008 | Bielmeier et al. |
| 7,342,999 | B2 | 3/2008 | Johansson et al. |
| 7,344,428 | B2 | 3/2008 | Ransil et al. |
| 7,349,725 | B2 | 3/2008 | Tsujita |
| 7,349,858 | B1 | 3/2008 | McGrady et al. |
| 7,350,626 | B2 | 4/2008 | Lence et al. |
| 7,356,123 | B2 | 4/2008 | Mollus |
| 7,359,649 | B2 | 4/2008 | Itoh et al. |
| 7,366,280 | B2 | 4/2008 | Lounsberry |
| 7,366,676 | B2 | 4/2008 | Evertsz |
| 7,366,703 | B2 | 4/2008 | Gray et al. |
| 7,366,904 | B2 | 4/2008 | Roh et al. |
| 7,368,741 | B2 | 5/2008 | Melnychuk et al. |
| 7,370,534 | B2 | 5/2008 | Lasser et al. |
| 7,371,240 | B2 | 5/2008 | Pinczewski et al. |
| 7,372,985 | B2 | 5/2008 | So et al. |
| 7,375,358 | B1 | 5/2008 | Martin et al. |
| 7,379,190 | B2 | 5/2008 | Hill |
| 7,379,532 | B2 | 5/2008 | Kramp |
| 7,380,710 | B2 | 6/2008 | Brown |
| 7,382,634 | B2 | 6/2008 | Buchmann |
| 7,382,816 | B2 | 6/2008 | Ariga et al. |
| 7,382,906 | B2 | 6/2008 | Meier |
| 7,385,313 | B2 | 6/2008 | Chen |
| 7,386,150 | B2 | 6/2008 | Fleisher |
| 7,388,208 | B2 | 6/2008 | Deych |
| 7,388,311 | B2 | 6/2008 | Bhargava |
| 7,389,530 | B2 | 6/2008 | Raghunath et al. |
| 7,389,558 | B2 | 6/2008 | Hagleitner et al. |
| 7,389,912 | B2 | 6/2008 | Carlson et al. |
| 7,389,928 | B2 | 6/2008 | Lubow |
| 7,392,011 | B1 | 6/2008 | Jacomb-Hood |
| 7,395,711 | B2 | 7/2008 | Greenwood |
| 7,396,332 | B2 | 7/2008 | Taimisto et al. |
| 7,397,202 | B2 | 7/2008 | Sung |
| 7,397,516 | B2 | 7/2008 | Tsukamoto |
| 7,399,453 | B2 | 7/2008 | Kelley et al. |
| 7,400,701 | B1 | 7/2008 | Cason |
| 7,402,814 | B2 | 7/2008 | Vieux et al. |
| 7,403,119 | B2 | 7/2008 | Leyden |
| 7,403,766 | B2 | 7/2008 | Hodge |
| 7,404,085 | B2 | 7/2008 | Lacasse et al. |
| 7,404,297 | B2 | 7/2008 | Chen |
| 7,405,056 | B2 | 7/2008 | Lam et al. |
| 7,407,628 | B2 | 8/2008 | Fukushima et al. |
| 7,411,766 | B1 | 8/2008 | Huang et al. |
| 7,416,604 | B2 | 8/2008 | Ishibashi et al. |
| 7,417,734 | B2 | 8/2008 | Kanda |
| 7,419,467 | B2 | 9/2008 | Tsai |
| 7,420,151 | B2 | 9/2008 | Fengler et al. |
| 7,423,688 | B2 | 9/2008 | Uenaka |
| 7,423,933 | B2 | 9/2008 | Pierre |
| 7,424,091 | B2 | 9/2008 | Park et al. |
| 7,426,037 | B2 | 9/2008 | Ostrovsky et al. |
| 7,426,260 | B2 | 9/2008 | Cantu et al. |
| 7,428,048 | B1 | 9/2008 | Farkas et al. |
| 7,428,290 | B2 | 9/2008 | Nishide et al. |
| 7,429,735 | B2 | 9/2008 | Lueerssen et al. |
| 7,431,498 | B2 * | 10/2008 | Youngblood-Johnson ... 378/177 |
| 7,431,719 | B2 | 10/2008 | Altshuler et al. |
| 7,432,498 | B2 | 10/2008 | Capron et al. |
| 7,432,667 | B2 | 10/2008 | Callewaert et al. |
| 7,432,707 | B1 | 10/2008 | Boitano |
| 7,432,868 | B2 | 10/2008 | Webb et al. |
| 7,433,034 | B1 | 10/2008 | Huang |
| 7,433,042 | B1 | 10/2008 | Cavanaugh et al. |
| 7,433,445 | B2 | 10/2008 | Okada et al. |
| 7,433,455 | B1 | 10/2008 | Oran |
| 7,434,582 | B2 | 10/2008 | Eubank |
| 7,435,966 | B2 | 10/2008 | Vogtmeier et al. |
| 7,436,028 | B2 | 10/2008 | Yang et al. |
| 7,436,291 | B2 | 10/2008 | Sellars et al. |

| | | | | | | |
|---|---|---|---|---|---|---|
| 7,436,500 B2 | 10/2008 | Treado et al. | 7,456,899 B2 | 11/2008 | Tanimoto et al. | |
| 7,437,025 B2 | 10/2008 | Kychakoff et al. | 7,457,536 B2 | 11/2008 | Hamada et al. | |
| 7,437,409 B2 | 10/2008 | Danieli | 7,517,148 B2 * | 4/2009 | Ceisel et al. | 378/191 |
| 7,437,782 B1 | 10/2008 | Burns | 7,541,599 B2 * | 6/2009 | Moritake et al. | 250/472.1 |
| 7,438,685 B2 | 10/2008 | Burdette et al. | 7,563,026 B2 * | 7/2009 | Mandelkern et al. | 378/191 |
| 7,438,727 B2 | 10/2008 | Williams, III et al. | 7,684,544 B2 * | 3/2010 | Wilson | 378/102 |
| 7,439,909 B2 | 10/2008 | Van Toorenburg | 2002/0040186 A1 | 4/2002 | Souney et al. | |
| 7,440,108 B2 | 10/2008 | Beale et al. | 2002/0041652 A1 * | 4/2002 | Suuronen | 378/63 |
| 7,440,604 B2 | 10/2008 | Tsuji et al. | 2002/0188198 A1 | 12/2002 | Hong | |
| 7,443,141 B2 | 10/2008 | Ichimasa | 2003/0078498 A1 | 4/2003 | Lang et al. | |
| 7,443,640 B2 | 10/2008 | Sung | 2004/0015079 A1 | 1/2004 | Berger et al. | |
| 7,445,609 B2 | 11/2008 | Bunke et al. | 2004/0249271 A1 | 12/2004 | Besson et al. | |
| 7,445,938 B2 | 11/2008 | Angeley | 2005/0075907 A1 | 4/2005 | Rao | |
| 7,446,319 B2 | 11/2008 | Yanagita et al. | 2005/0085731 A1 | 4/2005 | Miller et al. | |
| 7,446,331 B2 | 11/2008 | Urbon et al. | 2005/0229698 A1 | 10/2005 | Beecroft et al. | |
| 7,446,868 B1 | 11/2008 | Higgs et al. | 2005/0248587 A1 | 11/2005 | Kamiyama et al. | |
| 7,446,882 B2 | 11/2008 | De Lega et al. | 2005/0288569 A1 | 12/2005 | Battle et al. | |
| 7,447,911 B2 | 11/2008 | Chou et al. | 2006/0098779 A1 | 5/2006 | Turner | |
| 7,449,690 B2 | 11/2008 | Nishiyama et al. | 2006/0153341 A1 | 7/2006 | Guyonnet et al. | |
| 7,450,174 B2 | 11/2008 | Watanabe et al. | 2006/0235724 A1 | 10/2006 | Rosenthal | |
| 7,450,241 B2 | 11/2008 | Zuluaga | 2006/0264730 A1 | 11/2006 | Stivoric et al. | |
| 7,450,242 B2 | 11/2008 | Toida et al. | 2007/0016043 A1 | 1/2007 | Morris | |
| 7,452,103 B2 | 11/2008 | Kakiuchi | 2007/0050216 A1 | 3/2007 | Wright et al. | |
| 7,452,342 B2 | 11/2008 | Bonutti et al. | 2007/0140424 A1 | 6/2007 | Serceki | |
| 7,453,067 B2 | 11/2008 | Berger et al. | 2007/0145282 A1 | 6/2007 | Campbell | |
| 7,453,977 B2 | 11/2008 | DiBanca et al. | 2007/0189455 A1 | 8/2007 | Allison | |
| 7,454,183 B2 | 11/2008 | Moorti et al. | 2007/0189462 A1 | 8/2007 | Spahn | |
| 7,454,206 B1 | 11/2008 | Phillips et al. | 2007/0230659 A1 | 10/2007 | Turner | |
| 7,454,242 B2 | 11/2008 | Fear et al. | 2007/0269010 A1 | 11/2007 | Turner | |
| 7,454,794 B1 | 11/2008 | Hibberd | 2008/0317205 A1 * | 12/2008 | Inuga et al. | 378/97 |
| 7,454,806 B2 | 11/2008 | Koch et al. | 2010/0189224 A1 | 7/2010 | Bowers et al. | |
| 7,455,609 B2 | 11/2008 | Raghavan | 2010/0239069 A1 | 9/2010 | Bourdeaux et al. | |
| 7,455,640 B2 | 11/2008 | Suzuki et al. | | | | |
| 7,455,676 B2 | 11/2008 | Holsten et al. | * cited by examiner | | | |

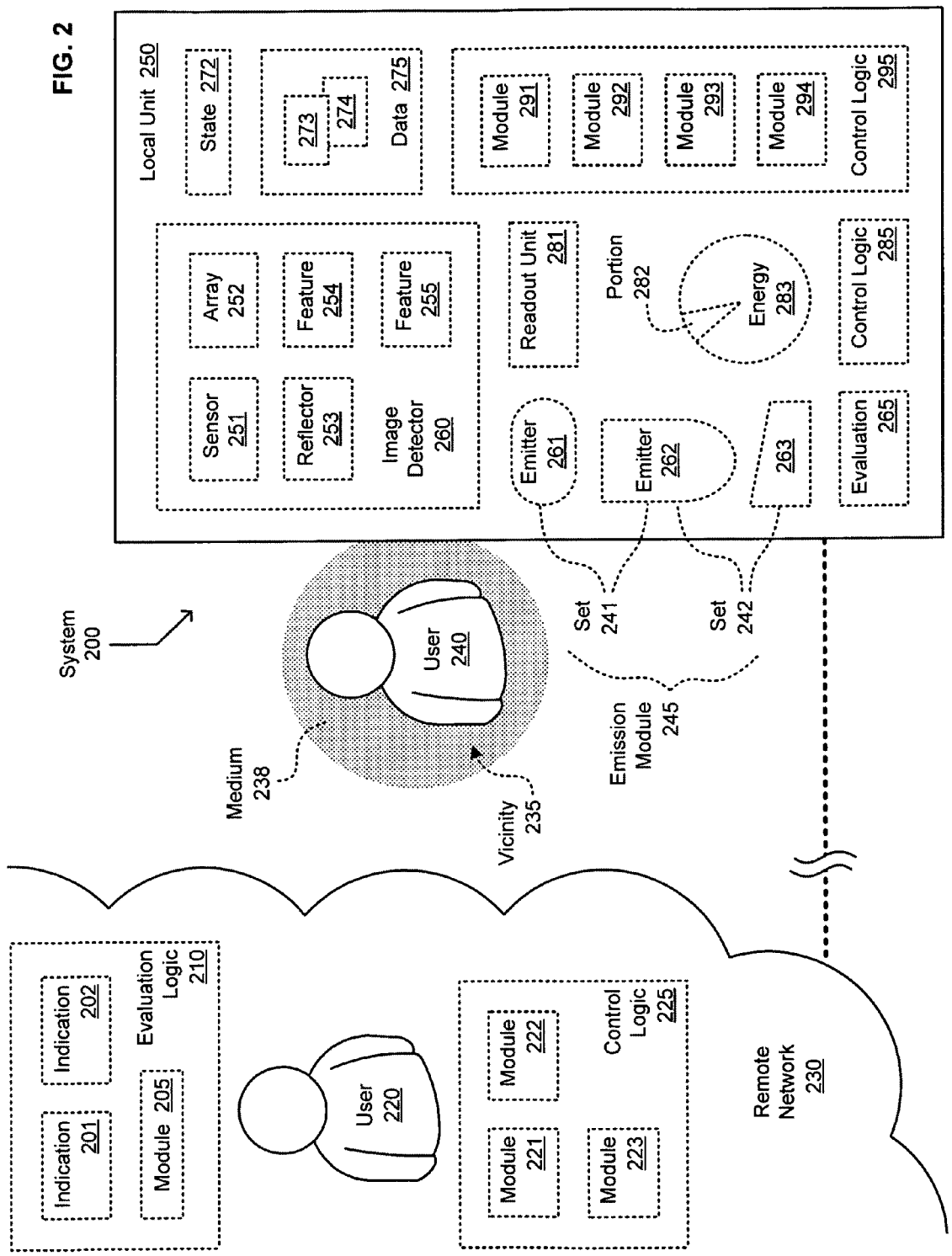

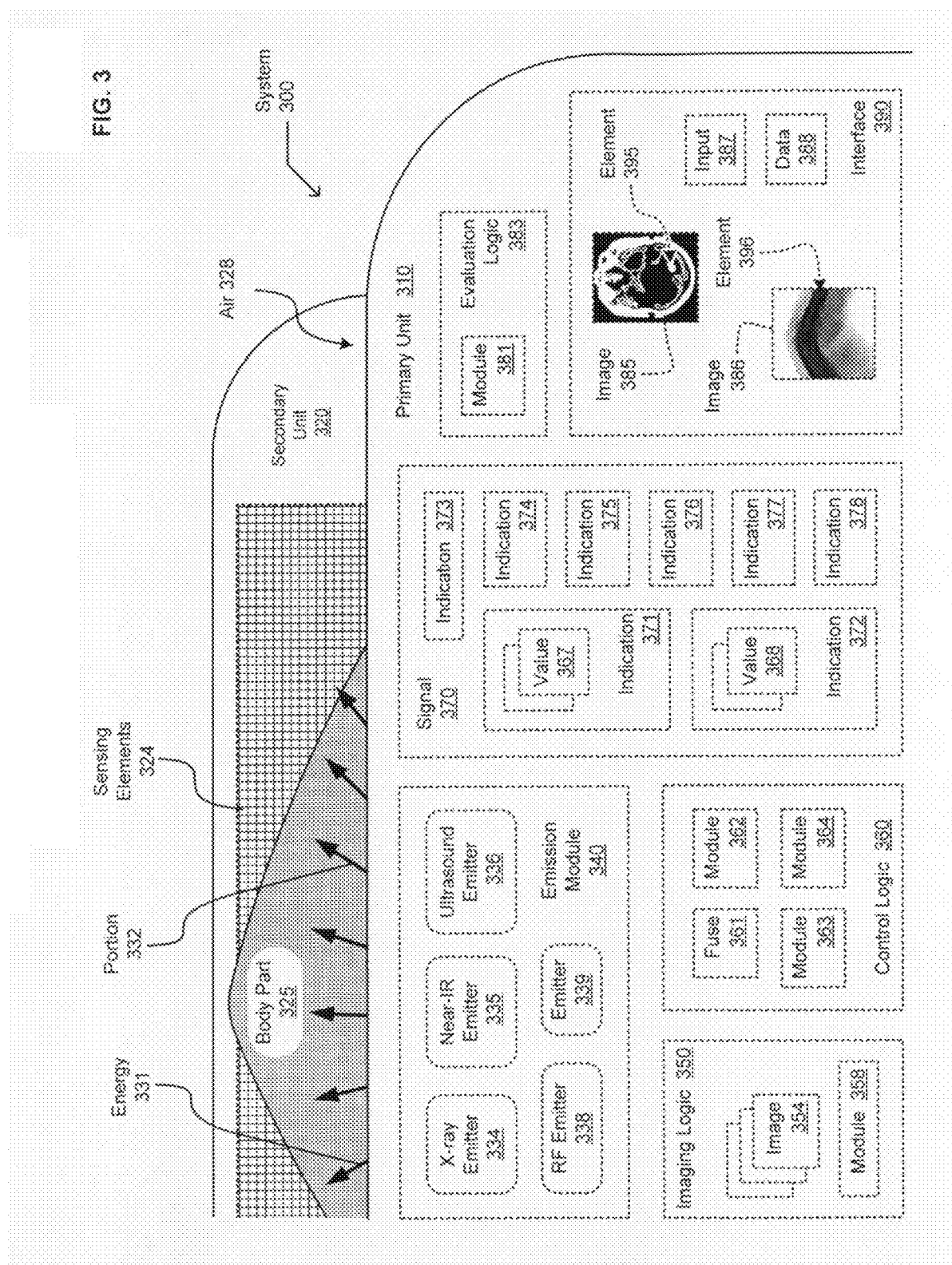

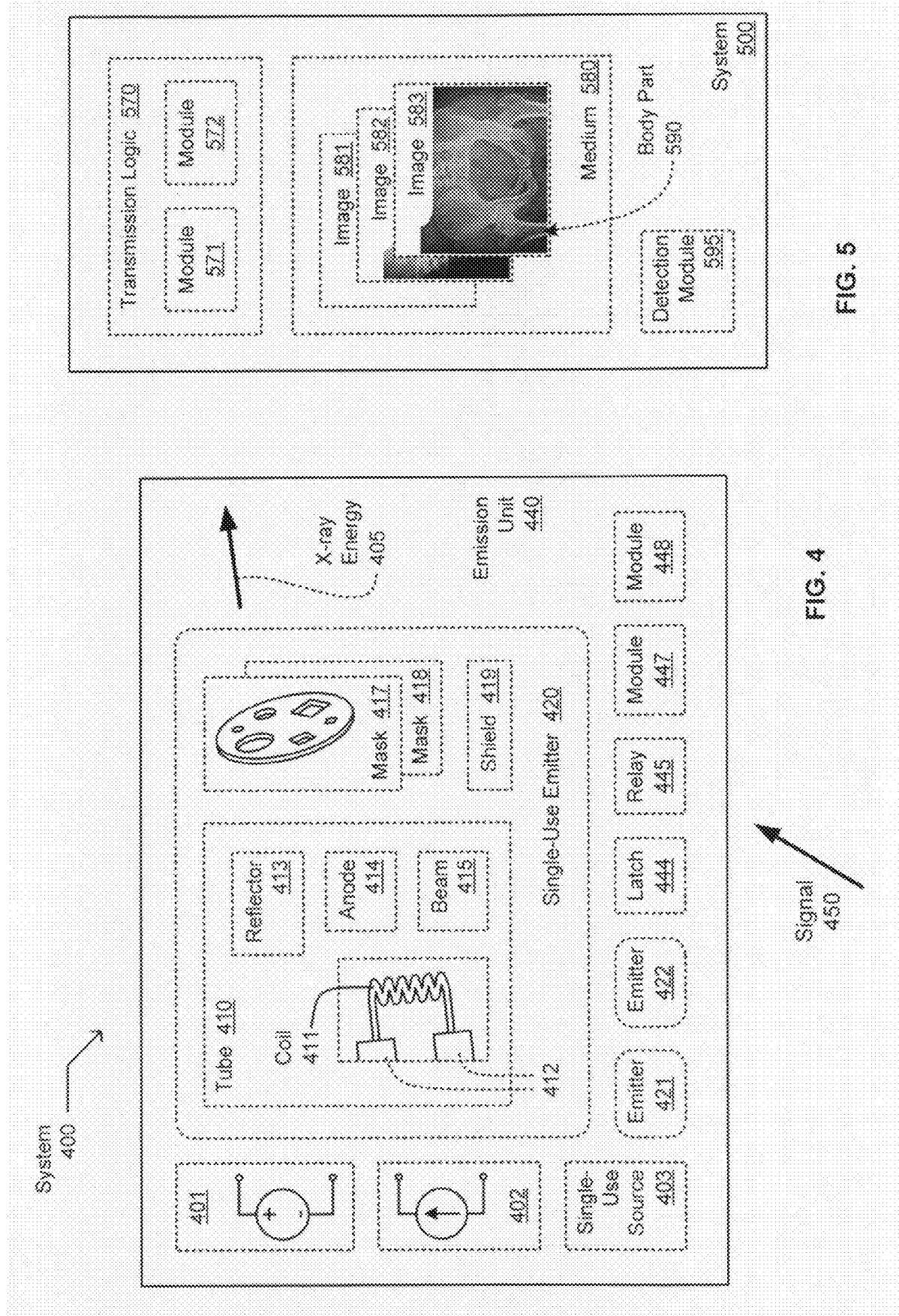

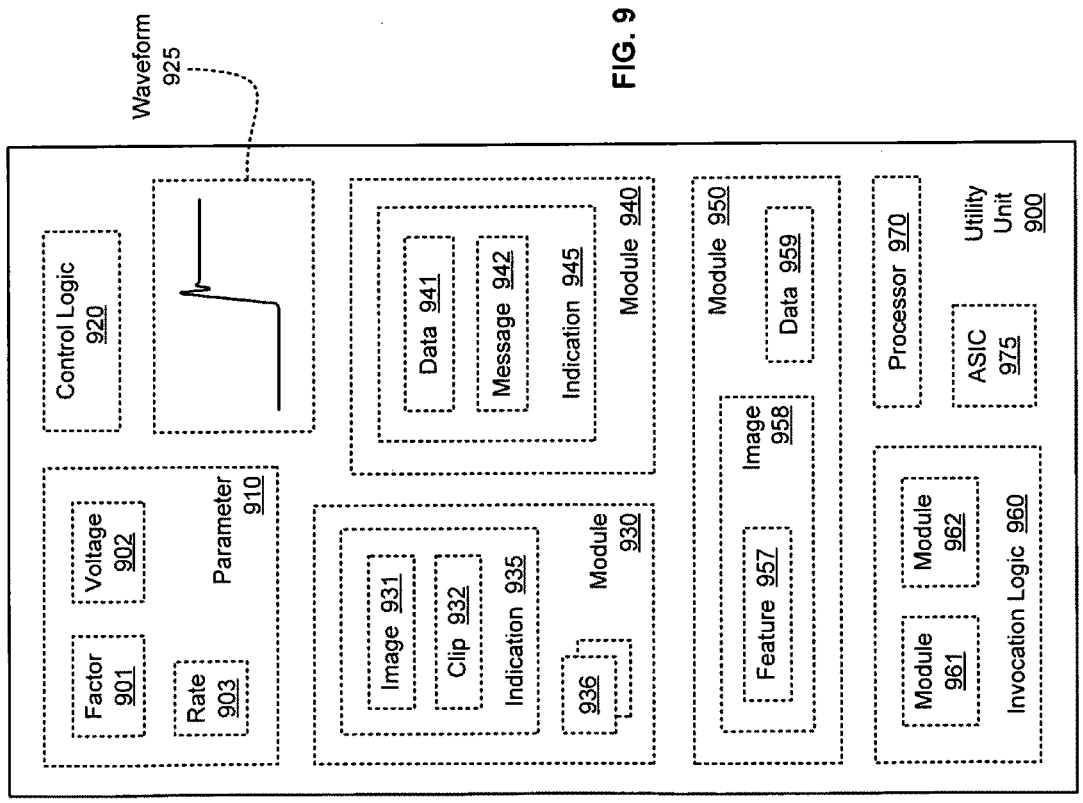

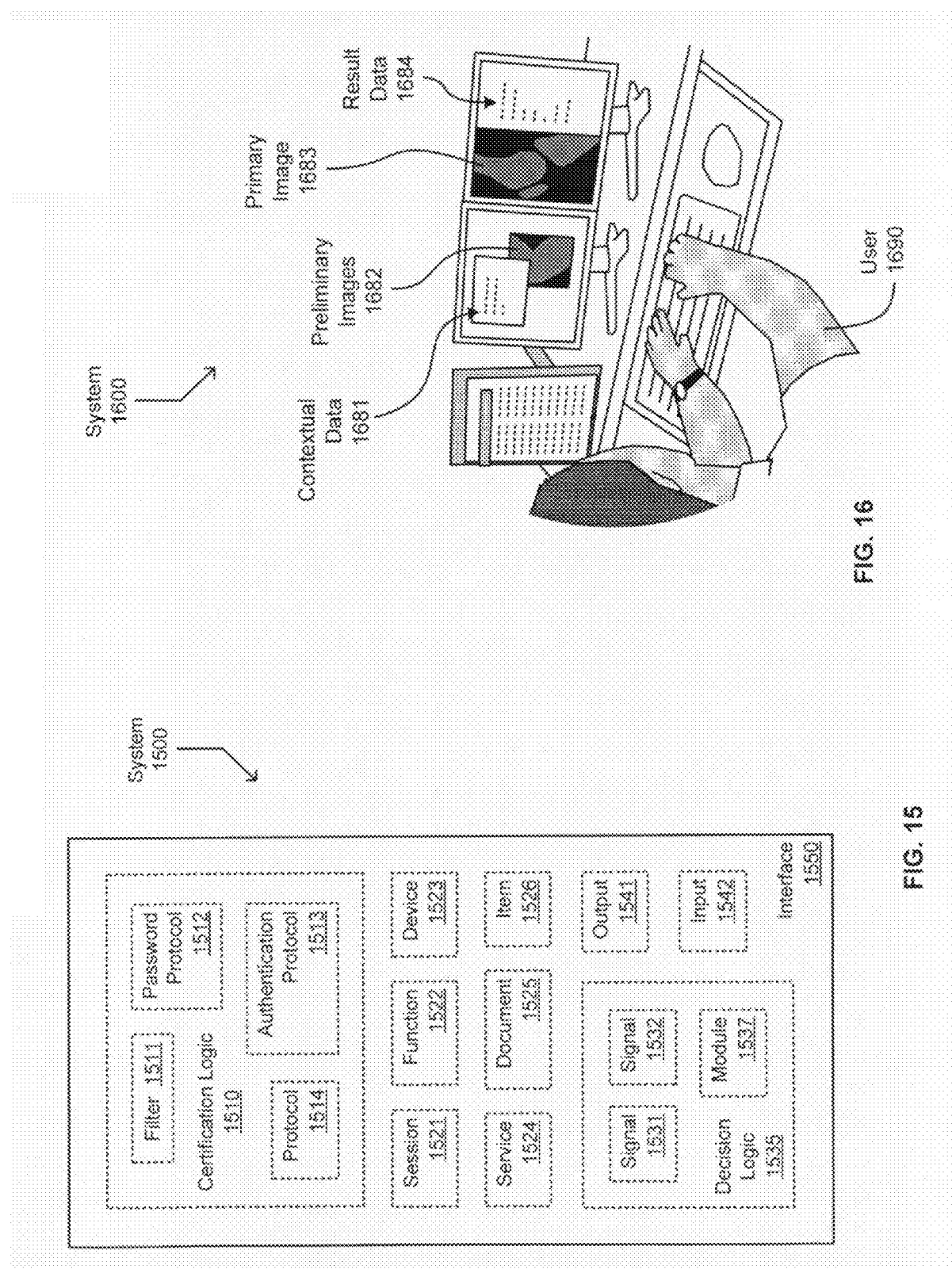

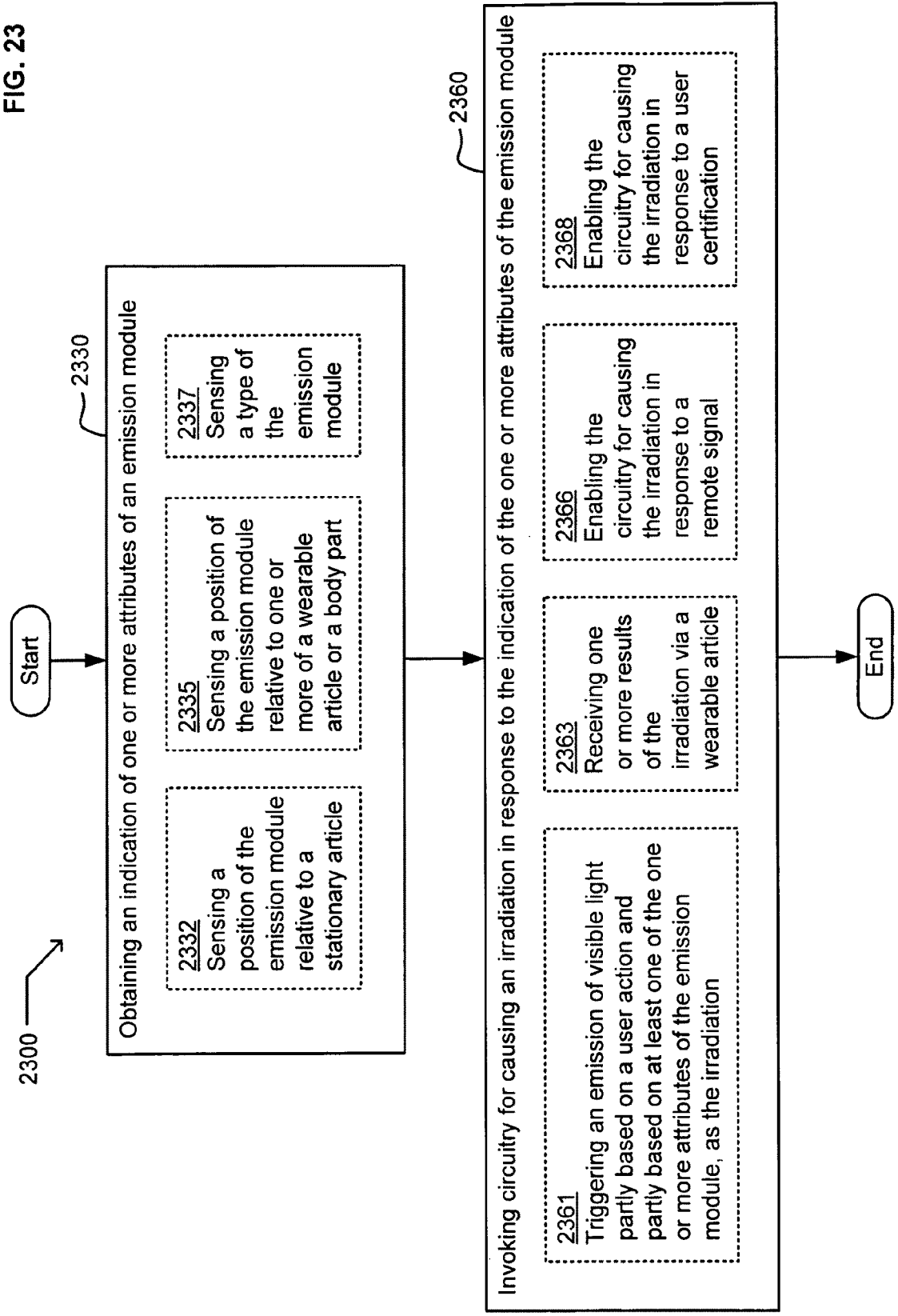

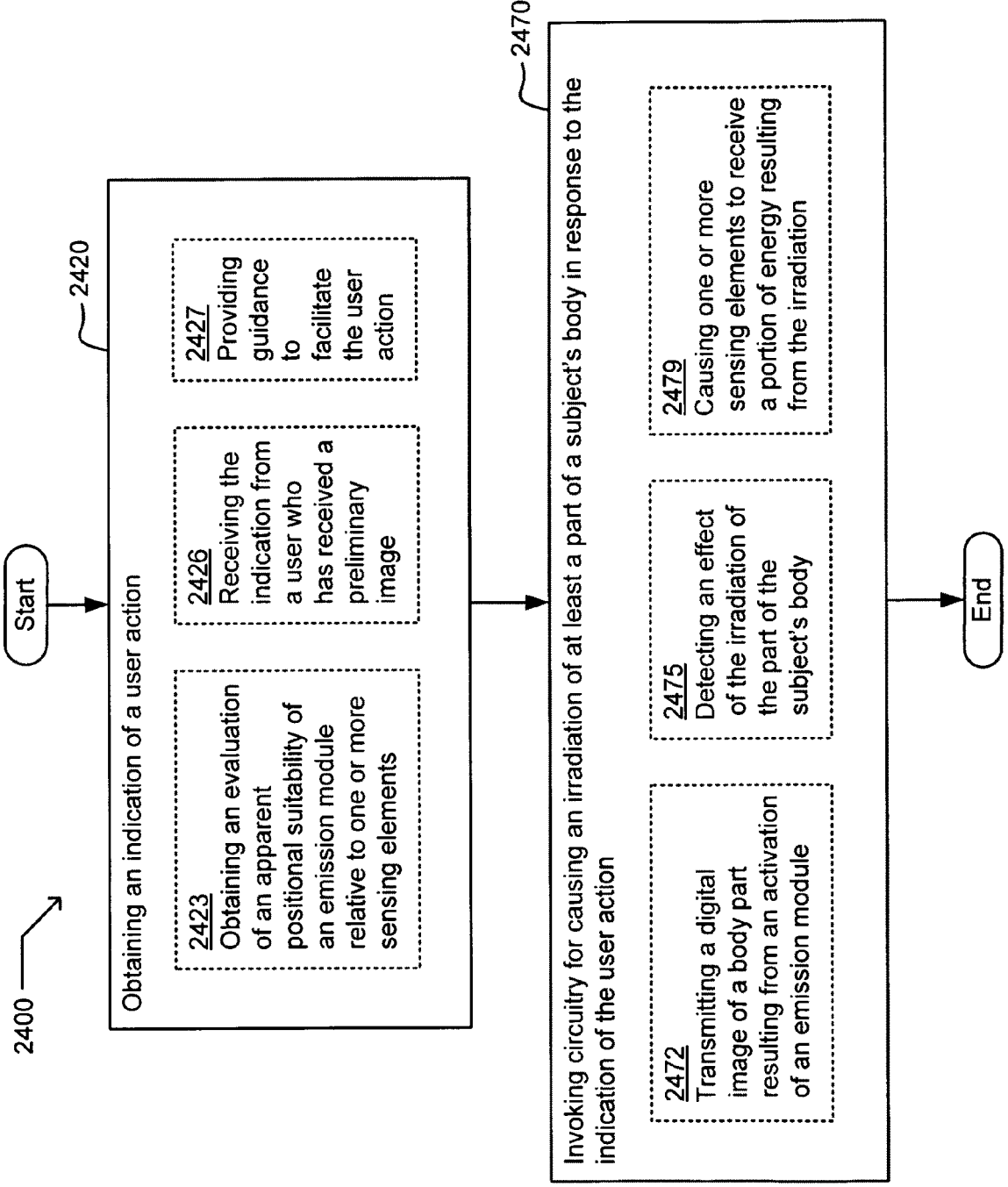

DIAGNOSTIC DELIVERY SERVICE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

Related Applications

1. For purposes of the USPTO extra-statutory requirements, the present application constitutes a continuation-in-part of U.S. patent application Ser. No. 12/322, 326, entitled DIAGNOSTIC DELIVERY SERVICE, naming Jeffrey A. Bowers, Roderick A. Hyde, Muriel Y. Ishikawa, Jordin T. Kare, Eric C. Leuthardt, Dennis J. Rivet, Elizabeth A. Sweeney and Lowell L. Wood, Jr. as inventors, filed 29, Jan. 2009, which is currently copending, or is an application of which a currently copending application is entitled to the benefit of the filing date.
2. For purposes of the USPTO extra-statutory requirements, the present application constitutes a continuation-in-part of U.S. patent application Ser. No. 12/322, 331, entitled DIAGNOSTIC DELIVERY SERVICE, naming Jeffrey A. Bowers, Roderick A. Hyde, Muriel Y. Ishikawa, Jordin T. Kare, Eric C. Leuthardt, Dennis J. Rivet, Elizabeth A. Sweeney and Lowell L. Wood, Jr. as inventors, filed 29, Jan. 2009, which is currently copending, or is an application of which a currently copending application is entitled to the benefit of the filing date.
3. For purposes of the USPTO extra-statutory requirements, the present application constitutes a continuation-in-part of U.S. patent application Ser. No. 12/322, 358, entitled DIAGNOSTIC DELIVERY SERVICE, naming Jeffrey A. Bowers, Roderick A. Hyde, Muriel Y. Ishikawa, Jordin T. Kare, Eric C. Leuthardt, Dennis J. Rivet, Elizabeth A. Sweeney and Lowell L. Wood, Jr. as inventors, filed 29, Jan. 2009, which is currently copending, or is an application of which a currently copending application is entitled to the benefit of the filing date.
4. For purposes of the USPTO extra-statutory requirements, the present application constitutes a continuation-in-part of U.S. patent application Ser. No. 12/322, 333, entitled DIAGNOSTIC DELIVERY SERVICE, naming Jeffrey A. Bowers, Roderick A. Hyde, Muriel Y. Ishikawa, Jordin T. Kare, Eric C. Leuthardt, Dennis J. Rivet, Elizabeth A. Sweeney and Lowell L. Wood, Jr. as inventors, filed 29, Jan. 2009, which is currently copending, or is an application of which a currently copending application is entitled to the benefit of the filing date.
5. For purposes of the USPTO extra-statutory requirements, the present application constitutes a continuation-in-part of U.S. patent application Ser. No. 12/322, 353, entitled DIAGNOSTIC DELIVERY SERVICE, naming Jeffrey A. Bowers, Roderick A. Hyde, Muriel Y. Ishikawa, Jordin T. Kare, Eric C. Leuthardt, Dennis J. Rivet, Elizabeth A. Sweeney and Lowell L. Wood, Jr. as inventors, filed 29, Jan. 2009, which is currently copending, or is an application of which a currently copending application is entitled to the benefit of the filing date.
6. For purposes of the USPTO extra-statutory requirements, the present application constitutes a continuation-in-part of U.S. patent application Ser. No. 12/322, 357, entitled DIAGNOSTIC DELIVERY SERVICE, naming Jeffrey A. Bowers, Roderick A. Hyde, Muriel Y. Ishikawa, Jordin T. Kare, Eric C. Leuthardt, Dennis J. Rivet, Elizabeth A. Sweeney and Lowell L. Wood, Jr. as inventors, filed 29, Jan. 2009, which is currently copending, or is an application of which a currently copending application is entitled to the benefit of the filing date.
7. For purposes of the USPTO extra-statutory requirements, the present application constitutes a continuation-in-part of U.S. patent application Ser. No. 12/322, 334, entitled DIAGNOSTIC DELIVERY SERVICE, naming Jeffrey A. Bowers, Roderick A. Hyde, Muriel Y. Ishikawa, Jordin T. Kare, Eric C. Leuthardt, Dennis J. Rivet, Elizabeth A. Sweeney and Lowell L. Wood, Jr. as inventors, filed 29, Jan. 2009, which is currently copending, or is an application of which a currently copending application is entitled to the benefit of the filing date.
8. For purposes of the USPTO extra-statutory requirements, the present application constitutes a continuation-in-part of U.S. patent application Ser. No. 12/322, 327, entitled DIAGNOSTIC DELIVERY SERVICE, naming Jeffrey A. Bowers, Roderick A. Hyde, Muriel Y. Ishikawa, Jordin T. Kare, Eric C. Leuthardt, Dennis J. Rivet, Elizabeth A. Sweeney and Lowell L. Wood, Jr. as inventors, filed 29, Jan. 2009, which is currently copending, or is an application of which a currently copending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

In one aspect, a method includes but is not limited to obtaining an indication of one or more attributes of an emission module and invoking circuitry for causing an irradiation in response to the indication of the one or more attributes of the emission module.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for obtaining an indication of one or more attributes of an emission module and circuitry for causing an irradiation in response to the indication of the one or more attributes of the emission module. In addition to the foregoing, other system aspects are described in the claims, drawings, and text forming a part of the present disclosure.

In one aspect, a method includes but is not limited to obtaining an indication of a user action and invoking circuitry for causing an irradiation of at least a part of a subject's body in response to the indication of the user action.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for obtaining an indication of a user action and circuitry for causing an irradiation of at least a part of a subject's body in response to the indication of the user action. In addition to the foregoing, other system aspects are described in the claims, drawings, and text forming a part of the present disclosure.

In some variants, a system includes an emission module having one or more activation-history-dependent features configured to prevent at least an unspecified user from being able to release more than a maximum amount of ionizing radiation energy via the emission module.

In some variants, a system includes first circuitry for transmitting a first image of a body part to a remote entity in response to an action by a local entity, second circuitry for causing an irradiation of the body part in response to the remote entity, and an imaging component configured to capture a second image of the body part in response to the remote entity.

In some variants, a system includes an electromagnetic radiation control module having at least a trigger operable for activating an ionizing radiation emitter and circuitry for resetting the electromagnetic radiation control module partly based on a certification of a user and partly based on an action by the user.

In some variants, a system includes an emission module operable for emitting electromagnetic energy, first circuitry for detecting an effect of the electromagnetic energy through a body part from the emission module, second circuitry for detecting an effect of other energy from the body part, and third circuitry for resetting the emission module partly based on a certification of a user and partly based on an action by the user.

In some variants, a system includes an ionizing radiation control module operable locally in response to one or more local user actions and circuitry for configuring the ionizing radiation control module locally in response to a remote signal.

In some variants, a system includes an emission module operable for emitting energy through a wireless medium, first circuitry for resetting the emission module partly based on a certification of a user and partly based on an action by the user, and a wearable article configured to support one or more sensing elements to receive a portion of the energy through a body part from the emission module.

In some variants, a system includes an emission module operable for emitting energy through a wireless medium, one or more sensing elements configured to receive a portion of the energy through a body part from the emission module, and circuitry for resetting the emission module partly based on a certification of a user and partly based on an action by the user.

In some variants, a system includes first circuitry for causing a use of a first energy emitter set and of at least a first image detection structure and second circuitry for causing a use of a second energy emitter set and of at least the first image detection structure partly based on a certification of a user and partly based on an action by the user.

In some variants, a system includes an emission module suitable for biological imaging and operable locally in response to one or more local user actions and circuitry for resetting the emission module locally in response to a remote signal.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to effect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 1-22 depict exemplary environments in which one or more technologies may be implemented.

FIGS. 23-24 depict a high-level logic flow of an operational process.

DETAILED DESCRIPTION

Figure 1:
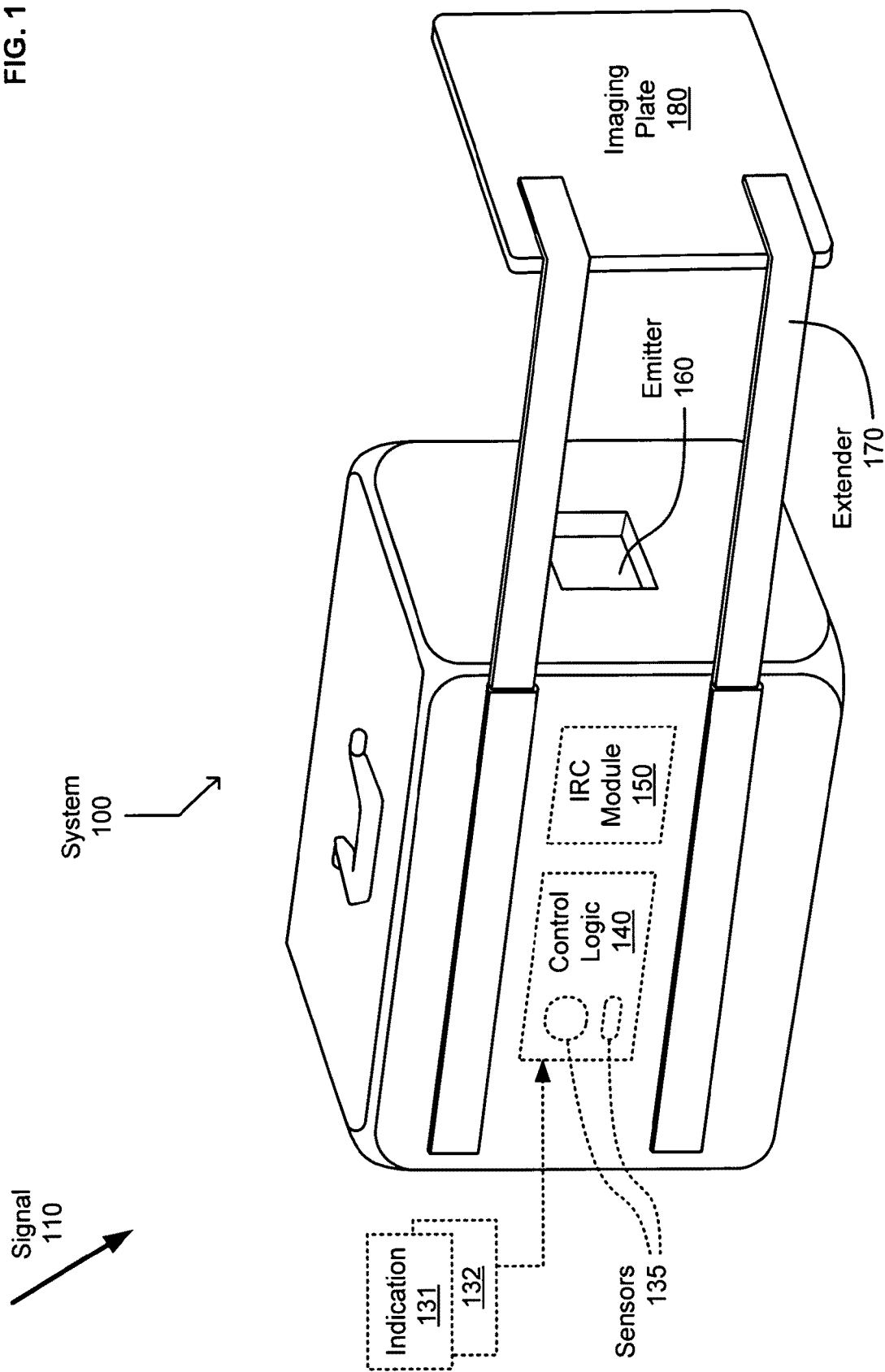

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

In a general sense, those skilled in the art will recognize that the various embodiments described herein can be implemented, individually and/or collectively, by various types of electromechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electromechanical as used herein is not necessarily limited to a system that has both electrical and mechanical actuation except as context may dictate otherwise.

In a general sense, those skilled in the art will also recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will further recognize that at least a portion of the devices and/or processes described herein can be integrated into an image processing system. A typical image processing system may generally include one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will likewise recognize that at least some of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

With reference now to FIG. 1, shown is a portable medical or veterinary system 100 in which one or more technologies may be implemented. It may (optionally) include one or more instances of a portable x-ray emission module or other ionizing radiation control (IRC) module 150 operable locally in response to one or more local user actions (manifesting as one or more indications 131, 132 of local gestures or vocal communication detectable by various sensors 135, e.g.). The embodiment further provides a controller board or other control logic 140 for resetting or otherwise configuring the IRC module 150 locally in response to a remote signal 110. (In some contexts, such "local" events refer to those in a common facility with or otherwise near an energy emitter and/or emission.) IRC module 150 may interact with a scanning or other emitter 160, for example, optionally configured for use with one or more imaging plates 180 supported in an appropriate position for imaging by one or more extenders 170. Other embodiments described below may likewise be implemented as a portable system containing one or more emission, control, detection, or other structural features.

In light of teachings herein, numerous existing techniques may be applied for selecting and positioning antennae, moreover, or other circuitry for receiving and processing a wireless signal in systems as described below without undue experimentation. See, e.g., U.S. Pat. No. 7,454,183 ("Method and system for antenna selection diversity with dynamic gain control"); U.S. Pat. No. 7,439,909 ("Antenna selection in a positioning system"); U.S. Pat. No. 7,432,868 ("Portable antenna positioner apparatus and method"); U.S. Pat. No. 7,397,516 ("Television broadcast receiver"); U.S. Pat. No. 7,392,011 ("Method and system for flexibly distributing power in a phased array antenna system"); U.S. Pat. No. 7,304,605 ("Method of calibrating an adaptive antenna array of a satellite navigation system"); U.S. Pat. No. 7,251,499 ("Method and device for selecting between internal and external antennas"); U.S. Pat. No. 7,180,470 ("Enhanced antenna stowage and deployment system"); U.S. Pat. No. 7,173,571 ("Portable antenna positioner apparatus and method"); U.S. Pat. No. 7,110,755 ("Information processing system, information processing method of information processing system, information processing apparatus, and information processing program"); U.S. Pat. No. 7,102,580 ("Antenna alignment devices"); U.S. Pat. No. 7,098,860 ("High performance low cost dipole antenna for wireless applications"); U.S. Pat. No. 7,027,007 ("Antenna mast and device for adjusting the orientation of an antenna"); U.S. Pat. No. 6,097,344 ("Mast mounting device for radar"); U.S. Pat. No. 5,841,397 ("Autotracking antenna system").

Numerous existing techniques may be likewise be applied for implementing various emitters suitable for imaging in structures and systems as described herein without undue experimentation. See, e.g., U.S. Pat. No. 7,452,103 ("Illuminating device for photoshooting"); U.S. Pat. No. 7,424,091 ("Combined panoramic, CT (computed tomography) and cephalometric photographing apparatus"); U.S. Pat. No. 7,336,763 ("Dental extra-oral x-ray imaging system and method"); U.S. Pat. No. 7,320,319 ("Medicant delivery system and method"); U.S. Pat. No. 7,274,766 ("Method and arrangement for three-dimensional medical X-ray imaging"); U.S. Pat. No. 7,206,375 ("Method and apparatus for implement XANES analysis"); U.S. Pat. No. 7,158,269 ("Scanner having a light beam incident position adjusting device"); U.S. Pat. No. 7,154,989 ("Radiological imaging apparatus"); U.S. Pat. No. 7,068,752 ("Method and arrangement for medical X-ray imaging"); U.S. Pat. No. 7,035,374 ("Optical device for directing x-rays having a plurality of optical crystals"); U.S. Pat. No. 6,947,522 ("Rotating notched transmission x-ray for multiple focal spots"); U.S. Pat. No. 6,668,040 ("Refractive X-ray arrangement"); U.S. Pat. No. 6,449,340 ("Adjustable x-ray collimator"); U.S. Pat. No. 6,139,499 ("Ultrasonic medical system and associated method").

Alternatively or additionally, various existing techniques may be applied for controlling energy emissions into a region, in light of these teachings, without undue experimentation. See, e.g., U.S. Pat. No. 7,419,467 ("Medical inspection device"); U.S. Pat. No. 7,396,332 ("Transducer with multiple resonant frequencies for an imaging catheter"); U.S. Pat. No. 7,370,534 ("Multiangle ultrasound imager"); U.S. Pat. No. 7,366,280 ("Integrated arc anode x-ray source for a computed tomography system"); U.S. Pat. No. 7,141,020 ("Portable 3D ultrasound system"); U.S. Pat. No. 7,102,123 ("Reflective imaging encoder"); U.S. Pat. No. 6,954,918 ("Integrated circuit cells"); U.S. Pat. No. 6,873,569 ("Method, system and probe for obtaining images"); U.S. Pat. No. 6,844,150 ("Ultrahigh resolution multicolor colocalization of single fluorescent probes"); U.S. Pat. No. 6,775,352 ("Method and system for implementing variable x-ray intensity modulation schemes for imaging systems"); U.S. Pat. No. 6,753,533 ("Electron beam apparatus and method of controlling same"); U.S. Pat. No. 6,612,982 ("Fully-swallowable endoscopic system"); U.S. Pat. No. 6,359,961 ("Apparatus and methods for stereo radiography including remote control via a network").

Numerous existing techniques may be applied, moreover, for configuring special-purpose circuitry or other features effective for disabling or otherwise limiting a local device or an operator's capabilities as described herein without undue experimentation. See, e.g., U.S. Pat. No. 7,455,609 ("Electrically variable transmission having three planetary gear sets and clutched motor/generators"); U.S. Pat. No. 7,454,794 ("Access control method"); U.S. Pat. No. 7,443,640 ("Apparatus for detecting arc fault"); U.S. Pat. No. 7,437,409 ("Limiting interaction between parties in a networked session"); U.S. Pat. No. 7,403,766 ("Telecommunication call management and monitoring system with voiceprint verification"); U.S. Pat. No. 7,399,453 ("Discharge reactor fuse link"); U.S. Pat. No. 7,389,912 ("Method and system for creating banking sub-accounts with varying limits"); U.S. Pat. No. 7,388,311 ("Redundant windings with current limiting means for electric machines"); U.S. Pat. No. 7,318,550 ("Biometric safeguard method for use with a smartcard"); U.S. Pat. No. 7,293,583 (""Countdown Timer" automatic water limiting supply shut off safety valve flo-control system"); U.S. Pat. No. 7,172,564 ("Automatic device for optimized muscular stimulation"); U.S. Pat. No. 7,156,709 ("Method for controlling the tilt position of a marine propulsion device"); U.S. Pat. No. 7,059,516 ("Person authentication system, person authentication method, information processing apparatus, and program providing medium"); U.S. Pat. No. 7,047,452 ("Method and system for detecting excessive use of a data processing system").

In some contexts, also, a variety of existing techniques may be applied for implementing a thermoluminescent screen, imaging optics, capture circuitry, or other such configurations suitable for detecting energy transmittance patterns or other structural features in systems as described herein without undue experimentation. See, e.g., U.S. Pat. No. 7,453,977 ("Variable resolution x-ray CT detector with target imaging capability"); U.S. Pat. No. 7,453,067 ("Detector with a scintillator, and imaging unit having such a detector"); U.S. Pat. No. 7,450,174 ("Two-dimensional image detector with disturbance-blocking buffer"); U.S. Pat. No. 7,449,690 ("Inspection method and inspection apparatus using charged particle beam"); U.S. Pat. No. 7,446,331 ("Apparatus for scanning stimulable phosphor medium"); U.S. Pat. No. 7,446,319 ("Semiconductor radiation detector and radiological imaging apparatus"); U.S. Pat. No. 7,440,604 ("Image detector for bank notes"); U.S. Pat. No. 7,440,108 ("Imaging spectrometer including a plurality of polarizing beam splitters"); U.S. Pat. No. 7,436,500 ("Near infrared chemical imaging microscope"); U.S. Pat. No. 7,433,445 ("Apparatus for and method of capturing radiation image"); U.S. Pat. No. 7,433,042 ("Spatially corrected full-cubed hyperspectral imager"); U.S. Pat. No. 7,433,034 ("Darkfield defect inspection with spectral contents"); U.S. Pat. No. 7,432,498 ("Method and apparatus for optically detecting and identifying a threat"); U.S. Pat. No. 7,429,735 ("High performance CCD-based thermoreflectance imaging using stochastic resonance"); U.S. Pat. No. 7,428,048 ("Imaging elastic scattering spectroscopy").

With reference now to FIG. 2, shown is another context in which one or more technologies may be implemented. As shown, a system 200 comprises a user 240 in a vicinity 235 of a local unit 250 operable for communicating to or from a remote network 230 (in another facility, e.g.) comprising one or more remote users 220. Remote user 220 may (optionally) use one or more modules 205 of evaluation logic 210, one or more modules 221, 222, 223 of control logic 225, or other such resources. Local unit 250 may include one or more instances of image detectors 260, emission modules 245, evaluations 265, states 272, images 273, 274 or other data 275, readout units 281, or modules 291, 292, 293, 294 of control logic 285, 295. Image detector 260 may include one or more instances of sensors 251 (or arrays 252), reflectors 253, or other such features 254, 255 as described herein. Emission module 245 may likewise (optionally) include one or more sets 241, 242 of emitters 261, 262, 263 operable for emitting energy 283 through air or other wireless media 238.

An embodiment provides (a) an emission module 245 operable for emitting energy 283 through a wireless medium 238, (b) one or more sensor arrays 252 or other sensing elements configured to receive a portion 282 of the energy 283 through a subject's body part from the emission module 245, and (c) one or more modules 294 of control logic 295 for resetting emission module 245 based on (an evaluation 265 or other result of) a certification of a user and an action by the user. This can occur, for example, in a context in which user 240 is the subject or otherwise has access to the subject, in which such certification manifests as indication 201, in which such action manifests as indication 202, and in which any other preconditions for triggering evaluation logic 210 to transmit evaluation 265 are met. In some variants, for example, one or more modules 205 are configured to respond affirmatively to an indication 201 that user 220 has remained active since logging on and to an indication 202 that user 220 has authorized a delegation of local control of emission module to user 240. (Such a delegation may be implemented or canceled in some variants, for example, by selectively enabling or disabling one or more local modules 293 of control logic 295.) Other variants are described below, for example, with reference to FIGS. 3 & 19.

In light of teachings herein, numerous existing techniques may (optionally) be applied for establishing a direct or indirect certification of a past or present user as described herein without undue experimentation. See, e.g., U.S. Pat. No. 7,447,911 ("Electronic identification key with portable application programs and identified by biometrics authentication"); U.S. Pat. No. 7,404,085 ("Authentication of handheld devices for access to applications"); U.S. Pat. No. 7,389,530 ("Portable electronic door opener device and method for secure door opening"); U.S. Pat. No. 7,366,904 ("Method for modifying validity of a certificate using biometric information in public key infrastructure-based authentication system"); U.S. Pat. No. 7,366,703 ("Smartcard internet authorization system"); U.S. Pat. No. 7,236,936 ("Security infusion pump with bar code reader"); U.S. Pat. No. 7,181,762 ("Apparatus for pre-authentication of users using one-time passwords"); U.S. Pat. No. 7,178,688 ("Portable medication dispenser"); U.S. Pat. No. 7,155,306 ("Medication administration system"); U.S. Pat. No. 7,028,180 ("System and method for usage of a role certificate in encryption and as a seal, digital stamp, and signature"); U.S. Pat. No. 6,981,147 ("Certification of multiple keys with new base and supplementary certificate types"); U.S. Pat. No. 6,234,969 ("Bone sonometry, densitometry and imaging"); U.S. Pat. No. 6,112,502 ("Restocking method for medical item dispensing system").

Numerous existing techniques may likewise be applied for generating a determination of whether a system and/or user state is suitable to proceed with an operation affecting a physical space in systems as described herein without undue experimentation. See, e.g., U.S. Pat. No. 7,445,609 ("Apparatus for controlling the delivery of medical fluids"); U.S. Pat. No. 7,437,782 ("Load sensing safety device for vertical lift"); U.S. Pat. No. 7,389,928 ("System and method of utilizing a machine readable medical marking for managing surgical procedures"); U.S. Pat. No. 7,349,725 ("Fluorescent image obtaining apparatus"); U.S. Pat. No. 7,342,368 ("Automated garage door closer"); U.S. Pat. No. 7,313,427 ("Laser diode optical transducer assembly for non-invasive spectrophotometric blood oxygenation"); U.S. Pat. No. 7,306,422 ("Dual function inboard barrier/bridgeplate assembly for wheelchair lifts"); U.S. Pat. No. 7,297,148 ("Surgical safety procedure and apparatus"); U.S. Pat. No. 7,191,941 ("Systems and methods for determining a need for authorization"); U.S. Pat. No. 7,108,663 ("Method and apparatus for cartilage growth stimulation"); U.S. Pat. No. 6,998,005 ("Method and apparatus for forming dye sublimation images in solid plastic"); U.S. Pat. No. 6,939,319 ("Process and device for single use, needle-free intradermal, subcutaneous, or intramuscular injections"); U.S. Pat. No. 6,864,478 ("Beam position monitoring for laser eye surgery"); U.S. Pat. No. 6,597,291 ("Garage door monitoring system"); U.S. Pat. No. 6,585,684 ("Automated system for the radiation treatment of a desired area within the body of a patient"); U.S. Pat. No. 6,487,804 ("Firearm with personal safety interlock mechanism"); U.S. Pat. No. 6,261,293 ("End cut apparatus for implanting spinal fusion device").

Numerous existing techniques may likewise be applied for associating an action with a user as described herein without undue experimentation. See, e.g., U.S. Pat. No. 7,454,206 ("Method and system with user identifiers that indicate session type"); U.S. Pat. No. 7,366,676 ("Method and system for in-service monitoring and training for a radiologic workstation"); U.S. Pat. No. 7,349,858 ("Method of dispensing and tracking the giving of medical items to patients"); U.S. Pat. No. 7,076,436 ("Medical records, documentation, tracking and order entry system"); U.S. Pat. No. 6,594,634 ("Method and apparatus for reporting emergency incidents").

Another embodiment provides (a) one or more modules 292 of control logic 285, 295 for causing a use of a set 241 of one or more energy emitters 261, 262 and of one or more features 254, 255 of image detector 260 and (b) one or more modules 221, 291 of control logic 225, 295 for causing a use of a set 242 of one or more energy emitters 262, 263 and of at least one image detector feature 254 partly based on a certification of one or more users 220, 240 who indicate willingness for such an emission. (In some embodiments, an inference may be "based on" a certification or other event if it indicates the event or otherwise results from the event, directly or indirectly.) This can occur, for example, in a context in which a skilled user 220 has had an opportunity to determine that local unit 250 is in an appropriate position and/or state 272 to proceed, in which a local or other evaluation 265 signifies such willingness manifested by a command or other such device-detectable action, and in which local unit 250 may degrade or harm people if used poorly and/or frequently. Various control logic 285, 295 of local unit 250 may simply receive such an evaluation 265, for example, from remote evaluation logic 210. Alternatively or additionally, one or more such modules 205 may transmit such an evaluation (contingently) in response to one or more indications 201 that user 220 been certified and has given one or more indications 202 permitting a local user 240 to activate an emission module 245 one or more times. Other variants are described below, for example, with reference to FIGS. 17-22.

In light of teachings herein, numerous existing techniques may be applied for enabling, disabling, and/or resetting a device via remote connection as described herein without undue experimentation. See, e.g., U.S. Pat. No. 7,385,313 ("Controller for on-off switching of power supplies"); U.S. Pat. No. 7,350,626 ("Power-on-reset of elevator controllers"); U.S. Pat. No. 7,171,568 ("Remote power control in a multi-node, partitioned data processing system"); U.S. Pat. No. 7,005,997 ("Remote emergency power shutoff and alarm system"); U.S. Pat. No. 6,787,937 ("Method of operating remote operated circuit breaker panel"); U.S. Pat. No. 6,479,981 ("Remote light indication fault indicator with a timed reset circuit and a manual reset circuit"); U.S. Pat. No. 6,346,880 ("Circuit and method for controlling an alarm"); U.S. Pat. No. 6,097,112 ("Electronic on/off switch for remote control model protected from inadvertent turn-off of its receiver").

Yet another embodiment provides (a) an emission module 245 effective for emitting x-ray or other imaging energy 283 toward user 240, (b) a readout unit 281 positioned for capturing a thermal or other image 273 indicating a portion 282 of the energy 283 (passing) through the body part from the emission module 245, and (c) one or more components configured to detect a digital image 274 or other data 275 indicative of such capture. This can occur, for example, in a context in which local unit 250 includes or otherwise interacts with one or more instances of one or more readout units 281, image detectors 260, or other detection units. In some variants, for example, readout unit 281 may comprise x-ray film or a thermoluminescent screen having a thin-film matrix of heaters or other such optical detection structures. Alternatively or additionally, such embodiments may include one or more modules 291-293 of control logic 295 operable for invoking one or more software-implemented or other reset protocols (of FIG. 12, e.g.) that reset some or all of emission module 245 responsive to data 275 or other output signals (remotely from user 240, e.g.) warranting such local control. Other variants are described below, for example, with reference to FIGS. 12-19.

With reference now to FIG. 3, shown is a system 300 in which one or more technologies may be implemented, comprising one or more primary units 310 separated from one or more secondary units 320 by a body part 325, air 328, or other wireless media. Primary unit 310 may use and/or include one or more instances of emission modules 340, modules 358 of imaging logic 350 (handling images 354, e.g.), fuses 361 or other modules 362, 363, 364 of control logic 360, signals 370, modules 381 of evaluation logic 383, or interfaces 390. Emission module 340 may likewise include one or more instances of x-ray emitters 334, near-infrared emitters 335, ultrasound emitters 336, visible light emitters, radio frequency emitters 338, or other emitters 339 as described below. In some variants, emission module 340 may permit various operational modes (for emitting more than one frequency or type of energy 331, for example, optionally via respective emitters). Alternatively or additionally, interface 390 may present, receive, or otherwise handle one or more images 385, 386; input 387; values 367, 368 or other indications 371-378 or data 388 as described below. Such data may likewise be handled by one or more sensing elements 324 operable for detecting a portion 332 of energy 331 passing through or around body part 325, for example, and transmitted to primary unit 310 or other entities as described below.

In light of teachings herein, for example, numerous existing techniques may be applied for configuring a brace or other wearable article effective for positioning a health-related component in a specific position relative to a living subject as described herein without undue experimentation. See, e.g., U.S. Pat. No. 7,320,319 ("Medicant delivery system and method"); U.S. Pat. No. 7,291,841 ("Device and system for enhanced SPECT, PET, and Compton scatter imaging in nuclear medicine"); U.S. Pat. No. 7,291,497 ("Medical device for analyte monitoring and drug delivery"); U.S. Pat. No. 7,194,298 ("Method and apparatus for trend detection in an electrocardiogram monitoring signal"); U.S. Pat. No. 7,147,372 ("Device and system for improved imaging in nuclear medicine and mammography"); U.S. Pat. No. 7,125,387 ("Ultrasonic apparatus for therapeutical use"); U.S. Pat. No. 6,745,071 ("Iontophoretic drug delivery system"); U.S. Pat. No. 6,467,905 ("Acquired pendular nystagmus treatment device"); U.S. Pat. No. 6,241,683 ("Phonospirometry for non-invasive monitoring of respiration"); U.S. Pat. No. 6,134,460 ("Spectrophotometers with catheters for measuring internal tissue"); U.S. Pat. No. 6,065,154 ("Support garments for patient-worn energy delivery apparatus"); U.S. Pat. No. 5,944,684 ("Wearable peritoneum-based system for continuous renal function replacement and other biomedical applications").

Numerous existing techniques may likewise be applied for configuring a reflector or diffraction grating, or otherwise for guiding emissions suitable for applications as described herein without undue experimentation. See, e.g., U.S. Pat. No. 7,450,241 ("Detecting vulnerable plaque"); U.S. Pat. No. 7,446,882 ("Interferometer for determining characteristics of an object surface"); U.S. Pat. No. 7,445,938 ("System and method for detecting presence of analytes using gratings"); U.S. Pat. No. 7,431,719 ("System for electromagnetic radiation dermatology and head for use therewith"); U.S. Pat. No. 7,426,037 ("Diffraction grating based interferometric systems and methods"); U.S. Pat. No. 7,404,297 ("Air conditioner with a light wave unit for auxiliary heating and sterilizing"); U.S. Pat. No. 7,395,711 ("System and technique for characterizing fluids using ultrasonic diffraction grating spectroscopy"); U.S. Pat. No. 7,344,428 ("Motion conversion mechanism for use with child containment structure"); U.S. Pat. No. 7,190,109 ("Illuminator for photodynamic therapy"); U.S. Pat. No. 7,137,712 ("Reflector system for determining position"); U.S. Pat. No. 7,088,901 ("Light guide apparatus and method for a detector array"); U.S. Pat. No. 6,932,807 ("Laser treatment apparatus"); U.S. Pat. No. 6,569,157 ("Removal of stratum corneum by means of light"); U.S. Pat. No. 6,507,638 ("X-ray imaging optical camera apparatus and method of use"); U.S. Pat. No. 6,400,741 ("Emission timing control apparatus for pulsed laser"); U.S. Pat. No. 6,366,737 ("External flash control system").

Alternatively or additionally, various existing techniques may be applied for combining a charging capacitor or other such energy dispensation element with one or more circuit breakers or other elements effective to present or otherwise control such dispensations as described herein without undue experimentation. See, e.g., U.S. Pat. No. 7,457,536 ("Flash device"); U.S. Pat. No. 7,443,141 ("Capacitor charging circuit, flash unit, and camera"); U.S. Pat. No. 7,403,119 ("Networked security system and method for monitoring portable consumer articles"); U.S. Pat. No. 7,382,816 ("Two-stage laser pulse energy control device and two-stage laser system"); U.S. Pat. No. 7,382,634 ("Voltage multiplier with charge recovery"); U.S. Pat. No. 7,368,741 ("Extreme ultraviolet light source"); U.S. Pat. No. 7,359,649 ("Infrared transmitter circuit and electronic device"); U.S. Pat. No. 7,336,018 ("Circuit configuration for charging and discharging a plurality of capacitive actuators"); U.S. Pat. No. 7,224,218 ("Pre-charge apparatus and method for controlling startup transients in a capacitively-coupled switching power stage"); U.S. Pat. No. 7,203,539 ("Apparatus and method for energy management in atrial defibrillator"); U.S. Pat. No. 7,119,502 ("Flashing discharge tube-use power supply and control method therefor"); U.S. Pat. No. 7,068,226 ("Pulsed plasma antenna"); U.S. Pat. No. 6,892,096 ("Implantable cardiac stimulating device with optimized demand"); U.S. Pat. No. 6,826,365 ("Battery saving flash charger control"); U.S. Pat. No. 6,662,792 ("Capacitor discharge ignition (CDI) system").

An embodiment provides a software-controlled module 363 or other circuitry for transmitting one or more images 385, 386 of a body part 325 to a remote entity (in remote network 30, e.g.) in response to an input 387 or other action by a local entity (user 220, e.g.) and an emission module 340 or other circuitry for irradiating the body part 325 in response to the remote entity. In some variants, the embodiment further provides one or more sensing elements 324, film, or other components for capturing another image of or other data 388 relating to the body part 325 in response to the remote entity. This can occur, for example, in a context in which local unit 250 implements one or more instances of system 300, in which such remote entities are highly skilled and/or specialized, and in which signal 370 includes one or more indications 374 that such a preliminary image 386 contains suitable alignment and/or subject matter. Alternatively or additionally, such transmissions may be made contingent upon a request or other decision, for example, by a local user, a module 381 configured for image recognition, or some other entity capable of sifting out clearly-suitable or clearly-unsuitable elements 396 of a preliminary image 386.

In light of teachings herein, numerous existing techniques may be applied for selecting and implementing an imaging protocol in response to a preliminary image or other indication of a symptom, body part, or other such parameters as described herein without undue experimentation. See, e.g., U.S. Pat. No. 7,382,906 ("Method of determining the region of interest in images of skin prints"); U.S. Pat. No. 7,342,999 ("Method and apparatus for generation of a digital x-ray image of an examination subject"); U.S. Pat. No. 7,320,518 ("Ophthalmic apparatus"); U.S. Pat. No. 7,303,555 ("Imaging and therapeutic procedure for carpal tunnel syndrome"); U.S. Pat. No. 7,263,156 ("Method and apparatus to facilitate computerized tomography of relatively large objects"); U.S. Pat. No. 7,197,107 ("X-ray CT apparatus and X-ray CT method"); U.S. Pat. No. 6,885,885 ("Magnetic resonance imaging method and device"); U.S. Pat. No. 6,816,564 ("Techniques for deriving tissue structure from multiple projection dual-energy x-ray absorptiometry"); U.S. Pat. No. 6,529,280 ("Three-dimensional measuring device and three-dimensional measuring method"); U.S. Pat. No. 6,383,135 ("System and method for providing self-screening of patient symptoms"); U.S. Pat. No. 6,192,105 ("Method and device to calibrate an automatic exposure control device in an x-ray imaging system").

Another embodiment provides (a) an emission module 340 operable for emitting energy 331 suitable for imaging through air 328, tissue, or other wireless media and (b) one or more sensing elements 324 configured to receive a portion 332 of the energy 331 through a body part 325 from the emission module 340. It may likewise include one or more modules 362 of control logic 360 or other circuitry for resetting the emission module 340 partly based on a certification of a user (manifesting as indication 371, e.g.) and partly based on an action by the user (manifesting as indication 372, e.g.). This can occur, for example, in a context in which a third-party input or other value 367 signifies the occurrence of such certification and in which one or more preference-indicative values 368 signify the occurrence of one or more such users 240 signaling an activation or other preference. Such contexts may effectively be confirmed, for example, by an indication 375 that one or more preliminary images 385, 386 contain symptomatic or other identifiable elements 395, 396. In some variants, one or more such modules 364 may operate (to enable or disable emission module 340, e.g.) selectively in response to one or more of (a) an indication 376 of improper alignment with body part 325 and/or sensing elements 324, (b) an indication 377 of insufficient charge to activate emission module 340, or (c) an indication 378 that primary unit 310, secondary unit 320, or a user might not be ready.

Some variants combine one or more single-use x-ray emitters 334 or other such emission modules 340 configured to emit energy 331 suitable for imaging with one or more modules 358 of imaging logic 350 for generating and/or transmitting a digital image 354 of a body part 325 resulting from an activation of the single-use emission module. In some variants, primary unit 310 may include additional instances of emission modules 340, such as for facilitating a confirmation of proper alignment before and/or during image capture. This can occur, for example, in a context in which module 358 includes circuitry for detecting (or for receiving from secondary unit 320, e.g.) one or more images 354 depicting body part 325 in relation to primary unit 310 and/or secondary unit 320.

In some embodiments, a "single-use" component may be configured to perform its primary function just once. This can occur, for example, in a context in which fuse 361 is configured to open a current path through one or more instances of emission module 340 upon an activation of a primary emitter therein. In some variants, for example, a single-use emission module may also permit one or more iterations of coarse imaging or other secondary functions (while or before transmitting higher-energy radiation suitable for medical imaging, e.g.). Alternatively or additionally, some "single-use" components may be refurbished or otherwise reset by certified entities in some contexts as described herein.

With reference now to FIG. 4, shown is a system 400 in which one or more technologies may be implemented, comprising one or more emission units 440 or other such modules primarily configured for energy emission. One or more voltage sources 401, current sources 402, single-use energy sources 403, or other sources may be configured to activate single-use emitter 420 or other emitters 421, 422 as described herein. Single use emitter 420 may include a vacuum tube 410 containing a coil 411 (primarily a tungsten alloy, e.g.) powered by current source 402, for example, via (anodes 414 or other) terminals 412 suitable to form an electron beam 415. In some variants, coil 411 may also have a calibrated diameter, for example, small enough generally to ensure that a filament will burn out the first time coil 411 is activated. Alternatively or additionally, current source 402 may be configured to provide a current pulse (on the order of several amperes or more, e.g.) high enough to burn out almost any such filament.

As shown, electrons in beam 415 collide with anode 414 by virtue of voltage source 401 providing a voltage about 30 to 50 kilovolts higher than that of terminals 412. This may cause x-ray energy 405 to be emitted in a controllable fashion (controlled by one or more reflectors 413 or shields 419, e.g.). In some contexts, for example, x-rays traveling in undesired directions may be absorbed by a rotary aperture mask 417 or other such components, any of which may be adjustable or selectable to effect a desired energy distribution. In light of teachings herein, numerous existing techniques may be applied for emitting and directing x-rays or other ionizing radiation for various purposes as described herein without undue experimentation. See, e.g., U.S. Pat. No. 7,416,604 ("Nitride crystal, nitride crystal substrate, epilayer-containing nitride crystal substrate, semiconductor device and method of manufacturing the same"); U.S. Pat. No. 6,984,051 ("Multifaceted reflecting mirror, illumination optical system based on use of the same, and semiconductor exposure apparatus"); U.S. Pat. No. 6,909,774 ("Apparatus and methods for surficial milling of selected regions on surfaces of multilayer-film reflective mirrors as used in X-ray optical systems"); U.S. Pat. No. 6,373,916 ("X-ray CT apparatus"); U.S. Pat. No. 5,812,631 ("Method for manufacturing monolithic capillary X-ray lens a monolithic capillary X-ray lens and apparatus using same"); U.S. Pat. No. 5,669,708 ("Optical element, production method of optical element, optical system, and optical apparatus"); U.S. Pat. No. 5,606,165 ("Square anti-symmetric uniformly redundant array coded aperture imaging system"); U.S. Pat. No. 5,533,087 ("X-ray imaging system including brightness control"); U.S. Pat. No. 5,090,038 ("Stereoscopic X-ray apparatus"); U.S. Pat. No. 4,798,446 ("Aplanatic and quasi-aplanatic diffraction gratings"); U.S. Pat. No. 4,534,051 ("Masked scanning X-ray apparatus"); U.S. Pat. No. 4,207,470 ("Tire inspection system").

In some contexts, system 400 may likewise include an ionizing radiation control module 447, one or more emitters 422, or other such components of emission unit 440 operable for emitting energy (locally in response to one or more user actions, e.g.) and a latch 444, relay 445, or other circuitry for resetting one or more modules 447, 448 locally in response to a remote signal 450. (In some variants, "ionizing radiation" energy may include photons (a) having a wavelength up to 280 nanometers or (b) directly causing ionization in germs or other organisms.)

In light of teachings herein, numerous existing techniques may be applied for incorporating such limited-use modules or other state-dependent features effective for limiting an allocation as described herein without undue experimentation. See, e.g., U.S. Pat. No. 7,456,899 ("Imaging apparatus and control circuit of imaging device"); U.S. Pat. No. 7,436,028 ("One-time programmable read only memory and operating method thereof"); U.S. Pat. No. 7,433,455 ("Processing a communication session using a rules engine"); U.S. Pat. No. 7,407,628 ("Biosensor and method of manufacturing biosensor"); U.S. Pat. No. 7,389,558 ("Brush head for one time use"); U.S. Pat. No. 7,380,710 ("Payment card preloaded with unique numbers"); U.S. Pat. No. 7,342,398 ("Method, device and magnetic resonance tomography system for monitoring emitted RF energy"); U.S. Pat. No. 7,256,446 ("One time programmable memory cell"); U.S. Pat. No. 7,188,564 ("Stencil printer with a duplex printing capability"); U.S. Pat. No. 7,182,770 ("Needle positioning forceps"); U.S. Pat. No. 6,507,699 ("Photographic process and one-time use camera to prevent unauthorized recycling and/or reuse of the camera").

With reference now to FIG. 5, shown is a system 500 in which one or more technologies may be implemented. System 500 may, in some contexts, include software or other instances of modules 571, 572 of transmission logic 570, detection modules 595 (configured to monitor images 581, 582, 583 of package contents or body parts 590, e.g.), or other such logic or data on physical media 580. In some contexts, for example, an emission unit 440 operable for emitting x-ray energy 405 may include or otherwise interact with an instance of system 500 having a module 571 for transmitting a digital image 583 of a body part 590 resulting from an activation of emission unit 440.

In light of teachings herein, numerous existing "biological-imaging-emission modules" may be suitable for spectrometry, neuroimaging, tomography, encephalography, or other such modes of biological imaging as described herein without undue experimentation. See, e.g., U.S. Pat. No. 7,455,640 ("Ultrasonic diagnostic apparatus"); U.S. Pat. No. 7,454,242 ("Tissue sensing adaptive radar imaging for breast tumor detection"); U.S. Pat. No. 7,450,242 ("Optical tomography apparatus"); U.S. Pat. No. 7,438,685 ("Apparatus and method for registration, guidance and targeting of external beam radiation therapy"); U.S. Pat. No. 7,432,707 ("Magnetic resonance imaging with corrected intensity inhomogeneity");

U.S. Pat. No. 7,420,151 ("Device for short wavelength visible reflectance endoscopy using broadband illumination"); U.S. Pat. No. 7,397,886 ("Method and apparatus for soft-tissue volume visualization"); U.S. Pat. No. 7,379,532 ("ECG-based rotational angiography for cardiology"); U.S. Pat. No. 7,372,985 ("Systems and methods for volumetric tissue scanning microscopy"); U.S. Pat. No. 7,349,725 ("Fluorescent image obtaining apparatus"); U.S. Pat. No. 7,330,531 ("System for quantitative radiographic imaging"); U.S. Pat. No. 7,328,060 ("Cancer detection and adaptive dose optimization treatment system"); U.S. Pat. No. 7,317,821 ("Automatic abnormal tissue detection in MRI images"); U.S. Pat. No. 7,266,407 ("Multi-frequency microwave-induced thermoacoustic imaging of biological tissue"). Alternatively or additionally, in some variants, such modules may be configured for therapeutic or other non-imaging purposes.

Figure 6:
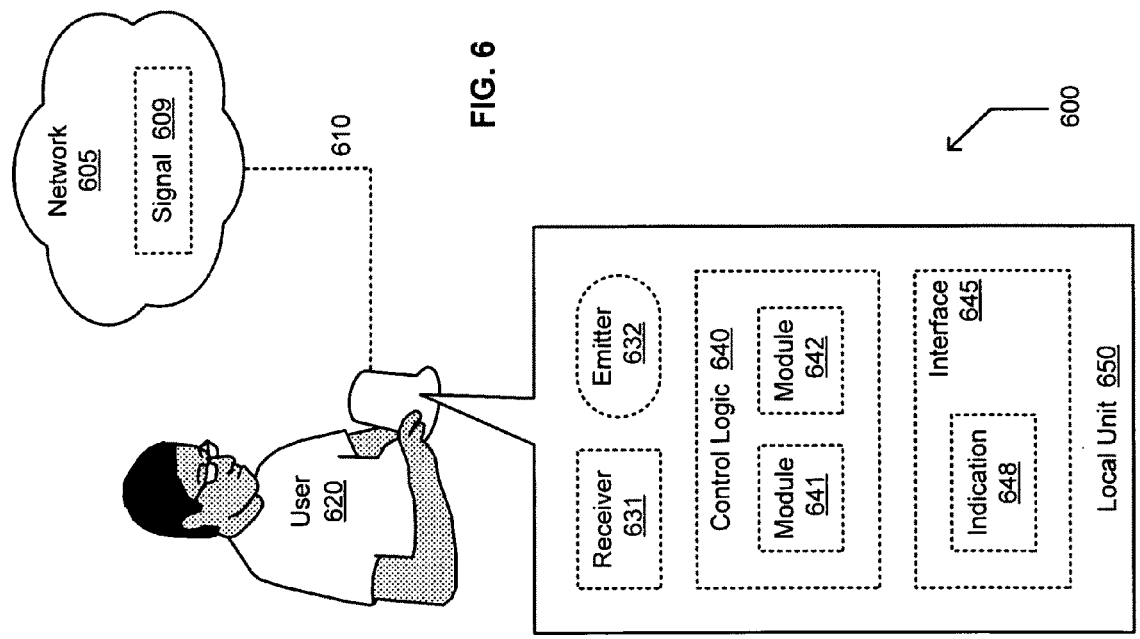

With reference now to FIG. 6, shown is a system 600 in which one or more technologies may be implemented for interacting with one or more networks 605 (via one or more signals 609) or users 620 (via one or more interfaces 645, e.g.). In some variants, a local unit 650 or other such emission module comprises one or more emitters 632 controlled by one or more modules 641 (in response to one or more indications 648 of local actions by user 620, e.g.). Alternatively or additionally, control logic 640 may include one or more other modules 642 for resetting such a local unit 650 in response to a remote signal 609. This can occur, for example, in a context in which such actions(s) are taken by an unskilled and/or unspecified local user, in which local unit 650 is suitable for biological imaging, and in which receiver 631 activates at least some control logic 640 in response to remote signal 609 (received from a remote specialist via linkage 610, e.g.).

In some embodiments, an "unspecified" user may include an unskilled and/or unknown user of a device. In some embodiments, such a user is "able to release" an amount of energy via a component in the absence of a design feature limiting the component to a smaller cumulative energy dispensation. A single-use flashbulb generally "prevents" a photographer from dispensing more than a single flash, for example, even if the flashbulb could be replaced by the photographer and/or refurbished by a flashbulb manufacturer. A conventional lightbulb filament similarly prevents most lamp users from emitting a nominal power level (in watts, e.g.) for much longer than the bulb's nominal operating life (in hours, e.g.). In some embodiments, moreover, a feature of a module may "prevent" an unspecified user from taking an action conditionally. A specialist or other user may reset or remove such features in some contexts, for example, to modify or circumvent such "prevention."

In some embodiments, an "activation history" may refer to any recorded or other detectable result of one or more activations. A fuse or other structural feature may be "dependent" on such a history, for example, if its state indicates to an observer or device whether or which such activation has apparently occurred.

In some embodiments, an "emission module" may include optical or other elements suitable to emit detectable energy through wireless media. In some contexts, such modules may likewise refer to special-purpose circuitry for controlling such emitters, remotely or otherwise, or to imaging or communication subsystems containing such modules.

In some embodiments, an emission module "suitable for" biological imaging may be configured to emit optical or other energy of a strength and uniformity sufficient to permit tissue imaging, subject or site identification, or other such useful functions within a region of interest. Various techniques are described herein for positioning an emission module in relation to tissue to be treated and/or imaged. Some such techniques may incorporate existing techniques for aligning an emitter with a target of interest with reference to a physical object, for example, by a skilled practitioner without undue experimentation. See, e.g., U.S. Pat. No. 7,455,676 ("Surgical stapling instruments including a cartridge having multiple staple sizes"); U.S. Pat. No. 7,313,840 ("Induction liquid pump and magnetic tank scrubber"); U.S. Pat. No. 7,241,296 ("Bipolar electrosurgical instrument for sealing vessels"); U.S. Pat. No. 7,238,180 ("Guided ablation with end-fire fiber"); U.S. Pat. No. 7,179,219 ("Incontinence treatment with urethral guide"); U.S. Pat. No. 6,932,818 ("Intramedullary nail-based bone fracture treatment"); U.S. Pat. No. 6,830,568 ("Guiding catheter system for ablating heart tissue"); U.S. Pat. No. 6,660,022 ("Rotor blade anchor and tool for installing same"); U.S. Pat. No. 6,616,671 ("Instrument and method for implanting an interbody fusion device"); U.S. Pat. No. 6,588,432 ("Tissue expander magnetic injection port").

In light of teachings herein, numerous existing techniques may likewise be applied for using a physical device to positioning a joint or other body part in an orientation suitable for treatment and/or diagnosis as described herein without undue experimentation. See, e.g., U.S. Pat. No. 7,454,806 ("Leg support arrangement for operating tables"); U.S. Pat. No. 7,452,342 ("Range of motion device"); U.S. Pat. No. 7,438,727 ("Locking shoulder joint"); U.S. Pat. No. 7,434,582 ("Oral appliance for maintaining stability of one or more aspects of a user's masticatory system"); U.S. Pat. No. 7,371,240 ("Method of arthroplasty on a knee joint and apparatus for use in same"); U.S. Pat. No. 7,322,951 ("Orthosis for correcting the position of a body joint"); U.S. Pat. No. 7,207,963 ("Shoulder brace"); U.S. Pat. No. 7,185,656 ("System for restraining head and neck movement"); U.S. Pat. No. 7,156,879 ("Femur fixture and set of femur fixtures"); U.S. Pat. No. 7,044,983 ("Positioning and buffering device for artificial knee joint").

Figure 7:
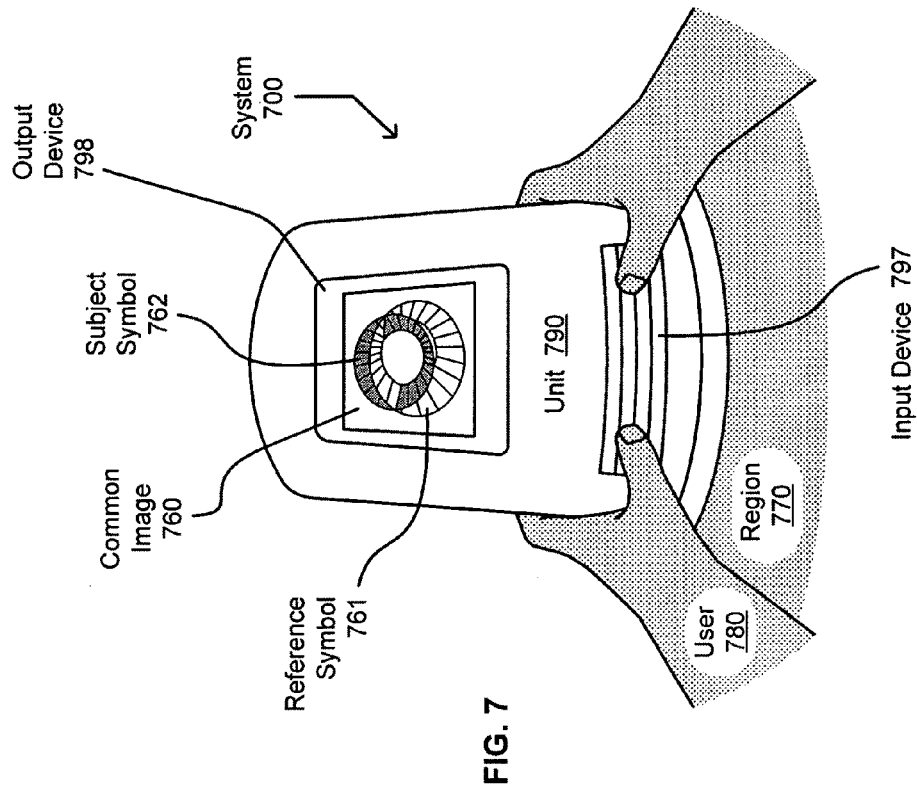

With reference now to FIG. 7, shown is a system 700 in which one or more technologies may be implemented for facilitating real time and other communications with a local user 780. Unit 790 includes one or more input devices 797 and one or more output devices 798 (displaying a common image 760 depicting a relative position of a reference symbol 761 and a subject symbol 762, e.g.). Such configurations may be useful, for example, for a local user 780 trying to position or scan emission and/or detection units as described herein relative to a target body part or other regions 770 of interest. Alternatively or additionally, a speaker or other output device 798 may be invoked (by a remote expert or other entity described herein, e.g.) to indicate (a) whether one or more physiological features are apparently recognizable in a digital image of region 770, (b) that an image is out of focus or insufficiently illuminated, (c) that region 770 is not the right target, or other such distillations.

Alternatively or additionally, a skilled practitioner will be able to apply various existing techniques for using an imaging detector and/or reference image to align device modules with a selected emission target as described herein without undue experimentation. See, e.g., See, e.g., U.S. Pat. No. 7,405,056 ("Tissue punch and tissue sample labeling methods and devices for microarray preparation, archiving and documentation"); U.S. Pat. No. 7,379,190 ("Stage alignment in lithography tools"); U.S. Pat. No. 7,327,452 ("Light beam apparatus and method for orthogonal alignment of specimen"); U.S. Pat. No. 7,324,842 ("Atlas and methods for segmentation and alignment of anatomical data"); U.S. Pat. No. 7,312,872 ("System and method for automated positioning of camera");

U.S. Pat. No. 7,170,968 ("CT scanner system and method for improved positioning"); U.S. Pat. No. 6,825,454 ("Automatic focusing device for an optical appliance"); U.S. Pat. No. 6,789,900 ("Scanning laser opthalmoscope optimized for selective retinal microphotocoagulation"); U.S. Pat. No. 6,546,276 ("Ultrasonic based detection of interventional medical device contact and alignment"); U.S. Pat. No. 5,769,790 ("Focused ultrasound surgery system guided by ultrasound imaging").

Figure 8:
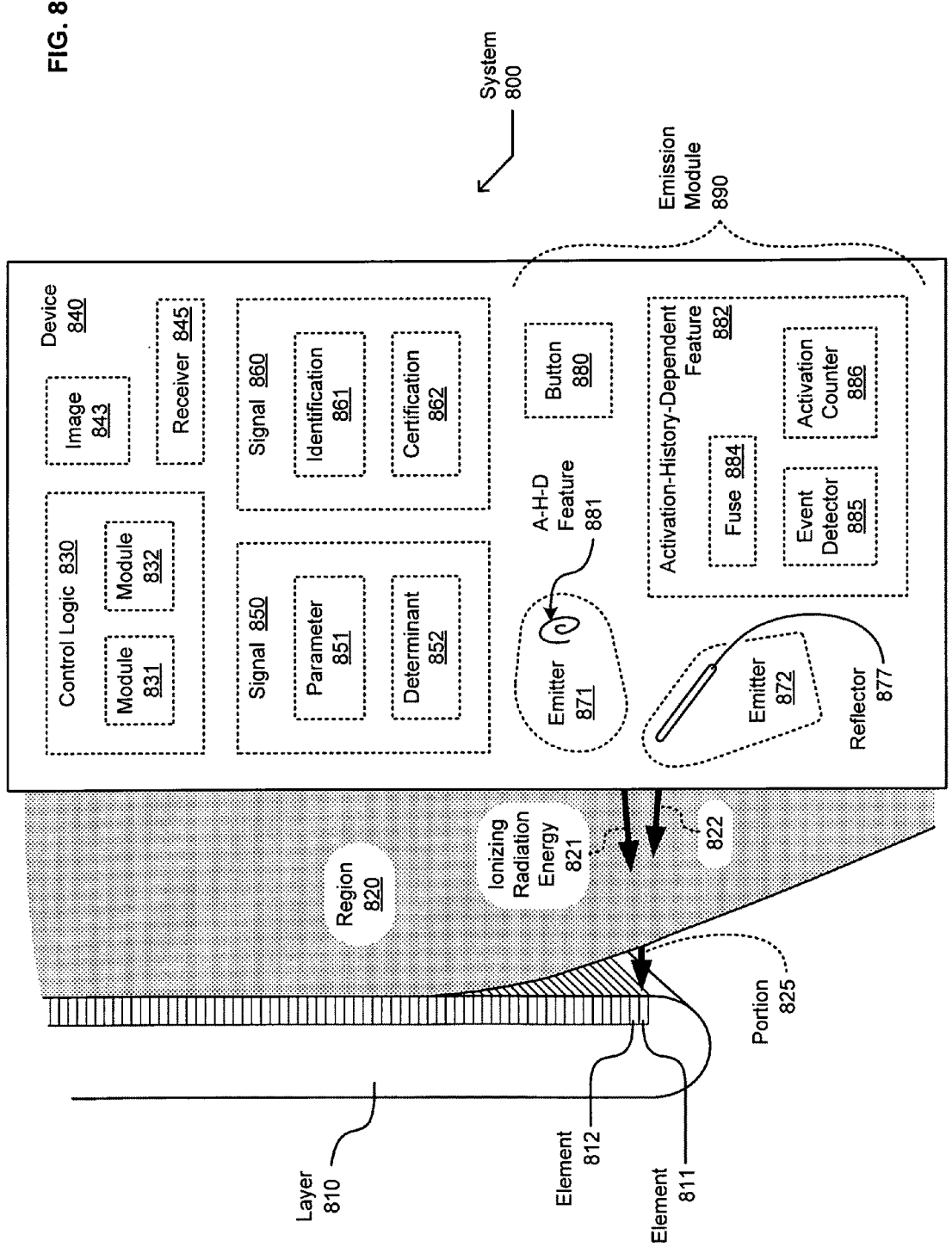

With reference now to FIG. 8, shown is a context in which one or more technologies may be implemented. System 800 may (optionally) comprise one or more device 840 operable for emitting ionizing radiation energy 821 or other energy 822. System 800 may further comprise one or more instances of control logic 830; receivers 845 (for handling images 843 from layer 810 or other signals 850, 860 from an optical receptor, e.g.); and emitters 871, 872 and other components of emission module(s) 890. In some contexts, for example, such an emission module 890 may include an ordinary reflector 877 or other feature that is (at least nominally) independent of an activation history of its emitter 872. Alternatively or additionally, an emission module 890 may include one or more event detectors 885, activation counters 886, analog circuitry, or other activation-history-dependent features 881, 882 configured to indicate cumulative emissions directly or indirectly for at least on emitter 871 or category of emissions.

An embodiment provides (a) an emission module 890, (b) a software-controlled module 832 or other special-purpose circuitry for resetting the emission module 890 in response to an activation signal 860, and (c) a wearable article (layer 810, e.g.) configured to position one or more sensing elements 811, 812 to receive a structure-indicative portion 825 of ionizing radiation energy 821 or other energy 822 emitted through a region 820 to be observed. This can occur, for example, in a context in which region 820 comprises a body part, in which activation-history-dependent feature 881 comprises circuitry for limiting a maximum exposure duration or other such control parameter 851 in response to an integrating photon detector (in emitter 871 or element 811, e.g.), and in which system 800 would otherwise permit an unskilled operator to expose region 820 to dangerous radiation levels by successive activations. In some contexts, module 831 may be configured to generate a reset and/or activation signal 850 based (a) upon a button 880 being pressed, (b) upon an identification 861 or other certification 862 of a person handling device 840, and/or (c) upon a user-specified control parameter 851 or other such determinant 852 as described herein. In some variants, for example, module 831 may operate upon detecting a later-occurring one of (1) certification 862 and (2) one or more emitters 871, 872 being sufficiently charged to emit a pulse suitable for imaging.

In some variants, a threshold or other determinant 852 may indicate a cumulative duration, a discrete number of activations, a score indicative of more than one type of activation, or other such subjective or other indicators. See, e.g., FIGS. 15-17. Alternatively or additionally, a control parameter 851 or other component of signal 850 may indicate a user code identifying a "budget" (in joules or milliseconds, e.g.) for each of several users of an emission module or a certification of any users that have not yet exhausted their "budgets." In some configurations, moreover, equivalent modes of control may be implemented by other structures, such as by similarly "metered" power supplies effective for enhancing an emission module's safety by limiting usage as described herein.

Another embodiment provides an emission module 890 having one or more fuses 884, activation counters, and/or other activation-history-dependent features 882 configured to prevent a less-skilled operator from being able to release more than an inherent maximum (on the order of 1 or 100 kilojoules, e.g.) of ionizing radiation energy 821 via the emission module 890. Such maxima may be appropriate, for example, in sterilization, security, or materials testing applications. In a context in which a photostimulable phosphor plate or other such detection layer 810 is used (for medical imaging in conjunction with a multidetector or electron beam computed tomography system, e.g.), a smaller effective emission threshold (on the order of 1 to 10 joules, e.g.) may be implemented.

With reference now to FIG. 9, shown is a context in which one or more technologies may be implemented. Systems as described herein may include or otherwise interact with one or more instances of utility units 900 positioned local to a subject of observation or other entity of interest as described herein. In some variants, for example, one or more local units 250, 650 may include control logic 920 or other circuitry operable for generating any of various emission pulse waveforms 925 in response to one or more voltages 902, emission frequencies, rates 903 of intensity change, polynomial weighting factors 901, or other such parameters 910. This can occur, for example, in a context in which the waveform 925 controls or comprises an emission of energy 283. Alternatively or additionally, control logic 640, 920 or other components may be implemented upon an Application-Specific Integrated Circuit 975 or other configuration suitable for responding to a signal 609 from a remote user 220 or other entity.

In some variants, utility unit 900 may likewise comprise one or more software-controlled modules 930 or other circuitry for transmitting a retinal or other facial image 931, a voice clip 932, or other personalizing indications 935 of a user 240 or other subject detected in a vicinity 235 of one or more emission modules 245 or other imaging modules that were or will be used upon the subject. Alternatively or additionally, an instance of utility unit 900 may include one or more hardware modules 940 or other circuitry for transmitting video data 941, an auditory or text message 942, or other personalizing indications 945 of a care provider responding remotely to a subject. Some variants may likewise include one or more instances of software-controlled modules 940 or other circuitry for transmitting video data 941, auditory or text messages 942, or other personalizing indications 945 of a care provider responding remotely to a subject.

In some contexts, a utility unit 900 may include one or more modules 961, 962 of invocation logic 960, processors 970, or similar circuitry (configured to execute or otherwise cause an invocation of a recognition module 950 or other resource, e.g.). In some variants, for example, a radiologist or other remote resource may respond to an evaluation request from module 962 by signaling whether any pathologies or other physiological features 957 are apparently recognizable in an image 958 or other data 959 from physical media 580; sensing elements 324, 811; or other such detection components as described below.

With reference now to FIG. 10, shown is a context in which one or more technologies may be implemented. Systems as described herein may include or otherwise interact with one or more instances of guidance units 1000 accessible to a paramedic or less-skilled user 1080. In some contexts, a device-implemented or other programmatic diagnosis protocol 1091, 1092 may include one or more operational sequences 1081, 1082, 1083 directing or permitting user 1080 to invoke various instances of sensors. In some contexts, for example, this permit user 1080 to interact with an expert user 220 or other remote resource via a headset 1094 or other interface 1095. Alternatively or additionally, guidance unit 1000 may include one or more instances of evaluation logic 1098 for evaluating positional or other situational data.

Figure 11:
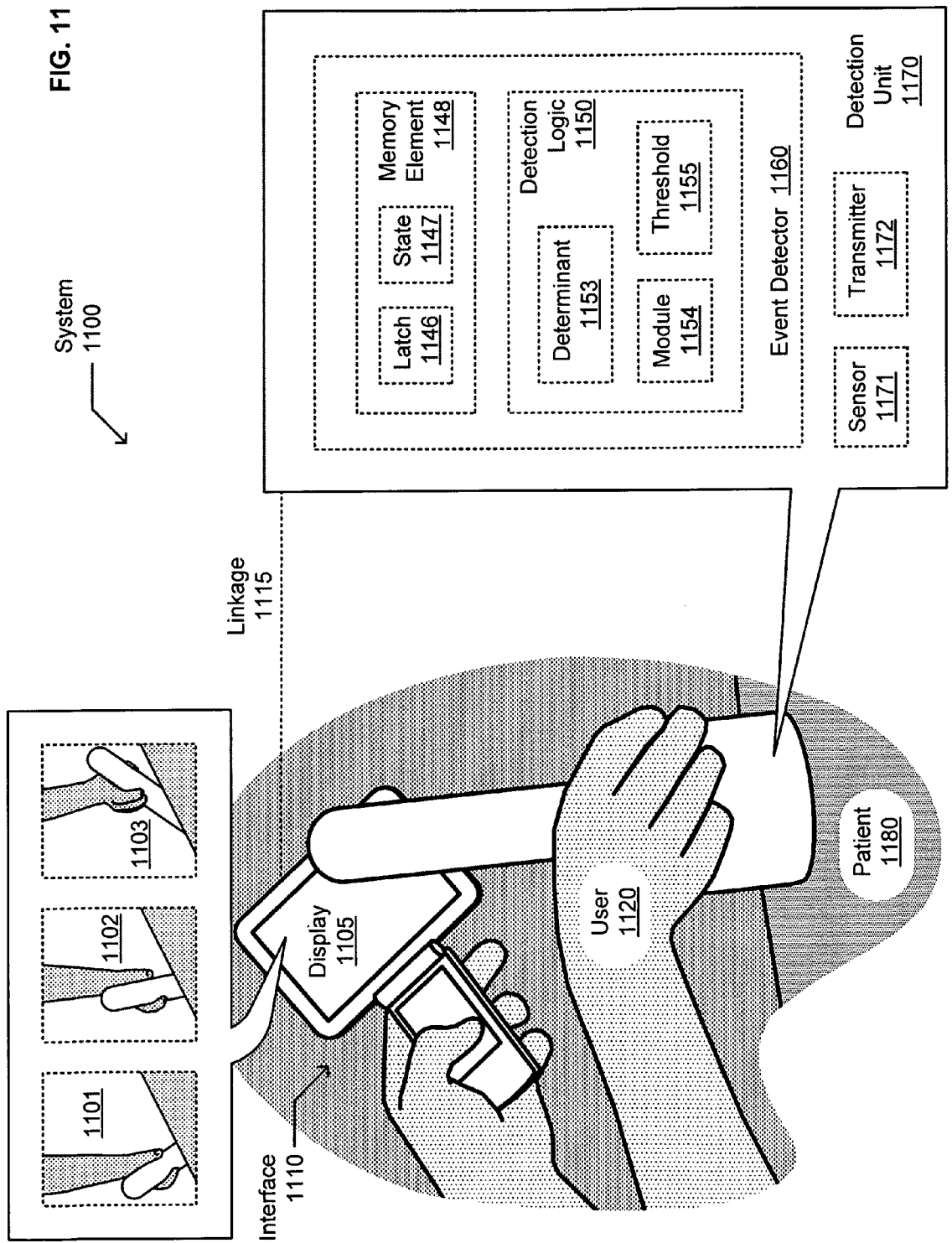

With reference now to FIG. 11, shown is a context in which one or more technologies may be implemented. System 1100 may comprise one or more instances of displays 1105 or other components of interfaces 1095, 1110 for interacting with a local user 1080, 1120, such as those described with reference to the embodiments above. In some variants, for example, display 1105 may present a video clip or other sequence of images 1101, 1102, 1103 identifying a preferable motion, position, or other protocol component for effective data acquisition relating to a patient 1180. This can occur, for example, in a context in which system 1100 includes one or more emission modules, event detectors 1160, sensors 1171, or other such detection units 1170. In some applications, for example, event detector 1160 may include one or more latches 1146 or other memory elements 1148 effective for indicating an event detector state 1147 resulting from one or more modules 1154 of detection logic 1150 applying a threshold 1155 or other analytical protocol to images, measurement data, or other such determinants 1153. In some variants, for example, detection unit 1170 may include one or more transmitters 1172 operable for indicating such states 1147 (via a wireless linkage 1115, e.g.) to a local interface 1110 or remote resource. Other such contexts are described above, for example, with reference to FIGS. 2 & 5-10.

In some variants, systems as described herein may include a local unit 650 or other (common) structure supporting an emitter, configuration logic or other emission control logic, and a local interface 648, 1110 for use in a proximity of a patient or other object of observation. Alternatively or additionally, local interfaces may include a display 1105 configured to present a facial image or video data (depicting a remote caregiver, e.g.) in a vicinity of such an emission module. (Such headsets 1094, detection units 1170, or other local units 250, 650 may likewise comprise one or more speakers/microphones to facilitate real-time interactions or auditory recordkeeping, in some implementations.)

Figure 12:
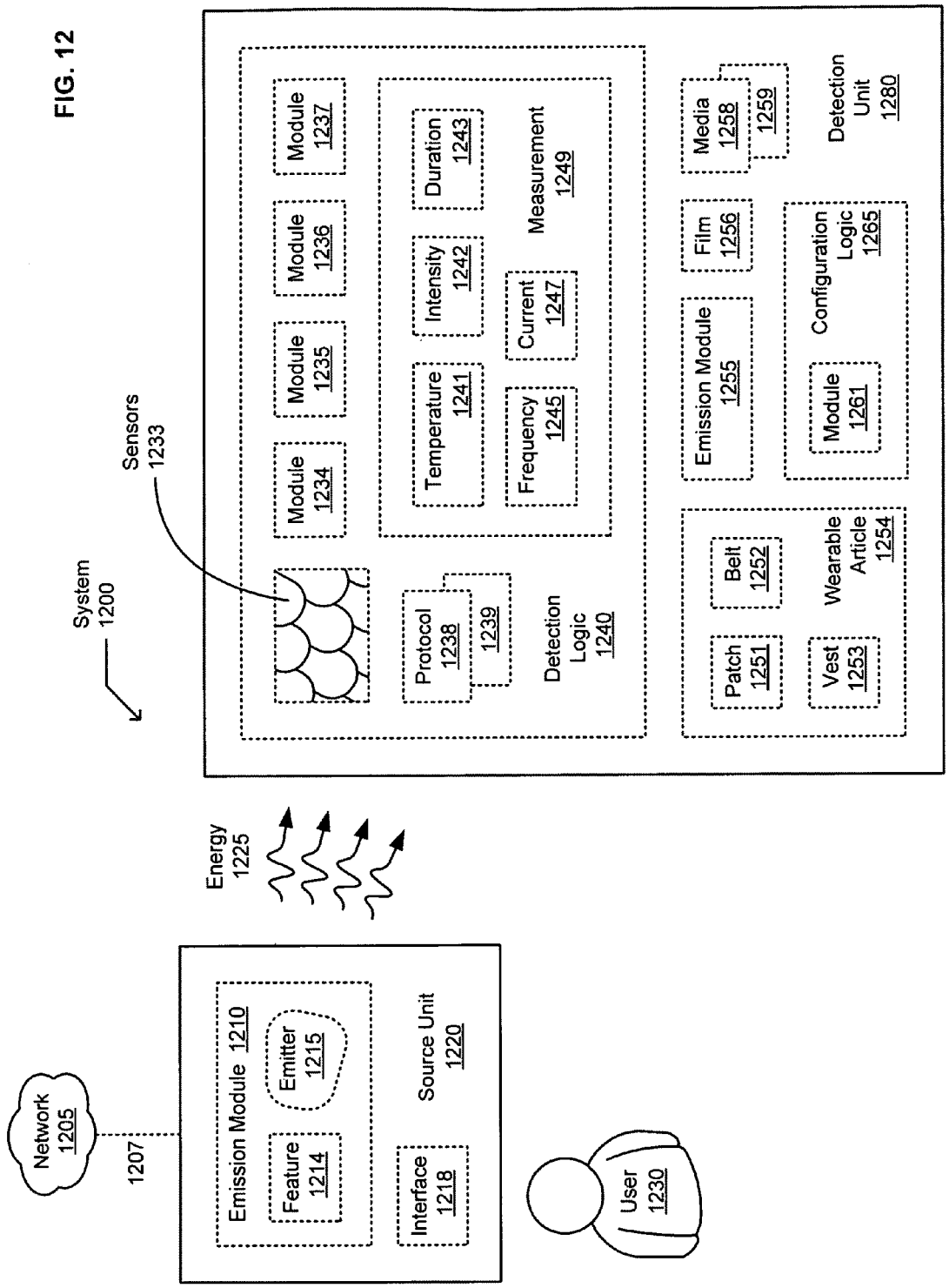

With reference now to FIG. 12 shown is a context in which one or more technologies may be implemented. System 1200 may comprise one or more instances of emitters 1215 or other components directly or otherwise operable by a user 1230 for transmitting energy 1225 through a region, such as for imaging or other functions in coordination with resources of network 1205. Alternatively or additionally, system 1200 may include a free-standing structure; a local unit 650 suitable to be held by a user; an adhesive patch 1251, belt 1252, vest 1253, or other wearable article 1254, a mounted article (for use on a door, e.g.), or other portable structure. In various configuration that will be apparent in light of these teachings, such structures may be configured to support one or more instances of detection logic 1240, emission modules 1255, energy detection or other optical elements (film 1256, e.g.), storage media 1258, presentation media 1259, or modules 1261 of configuration logic 1265. In some variants, for example, a suitably-positioned instance of detection logic 1240 may include arrayed or other sensors 1233, hardware-implemented or other protocols 1238, 1239, or other modules 1234, 1235, 1236, 1237 for obtaining measurements 1249 or other data useful for diagnoses. Other such contexts are described throughout this document.

An embodiment provides an emission module 1210 suitable for visible-spectrum or other biological imaging (in emitting energy 1225, e.g.) and operable locally in response to one or more inputs via interface 1218 or other actions by user 1230. This can occur, for example, in a context in which local unit 650 (of FIG. 6) includes (a) a receiver 631 and (b) software or other modules 642 comprising or controlling circuitry for resetting the emission module 1210 locally in response to a remote signal 609 (from network 1205 or detection unit 1280, e.g.). In some variants, for example, such a signal may contain or otherwise trigger a reset protocol by which module 642 resets a "remaining activations" counter or other such activation-history-dependent feature 1214 (to permit user 1230 to resume imaging, e.g.).

Another embodiment provides an emission module 1210 having one or more network linkages 1207 or other activation-history-dependent features 1214 configured to prevent user 1230 from being able to release more than about 10 to 100 kilojoules of ionizing radiation energy 1225 via the emission module 1210 (for emitting an amount of far-ultraviolet light effective for sterilizing an operating room or other such facility in response to a janitor's control activation, e.g., without being fatal to a human occupant thereof). In some variants, for example, such features may prevent user 1230 from being able to release more than a maximum (one the order of about 3 or 300 joules, e.g.) of ionizing radiation energy 1225 via the emission module 1210 (for emitting an amount of x-ray light sufficient for generating a series of x-ray images, e.g., via film slides or sensors 1233). Alternatively or additionally, a server or other resource in network 1205 may transmit a single-use or reset authorization in response to a history of activation by user 1230 or of source unit 1220. For many diagnostic applications, an activation-history-dependent feature 1214 may optionally be configured to prevent a less-skilled user from being able to release more than a maximum (on the order of 0.3 or 30 joules, e.g.) of ionizing radiation energy 1225. Alternatively or additionally, source unit 1220 may include a mechanical linkage with detection unit 1280 or other such feature to facilitate or confirm an appropriate relative position as described herein (as exemplified in FIG. 1, e.g.).

Some variants of the above-described embodiments, with reference to FIGS. 2-8 for example, can occur in a context in which (a) event detector 1160 includes a latch 1146 or other memory element 1148 having a state 1147 indicative of whether a determinant has crossed an emission-indicative threshold 1155 and in which (b) measurements 1249 or other determinants 1153 are obtained by one or more sensors 1233 or other event-responsive modules 1154, 1234 (of detection logic 1150, 1240, e.g.). In some variants, for example, emitters as described herein may manifest activation as one or more detectably higher-than-nominal temperatures 1241, intensities 1242, durations 1243, frequencies 1245, currents 1247, or other energy-indicative measurements 1249, control parameters, or other determinants obtained as described herein.

Figure 13:
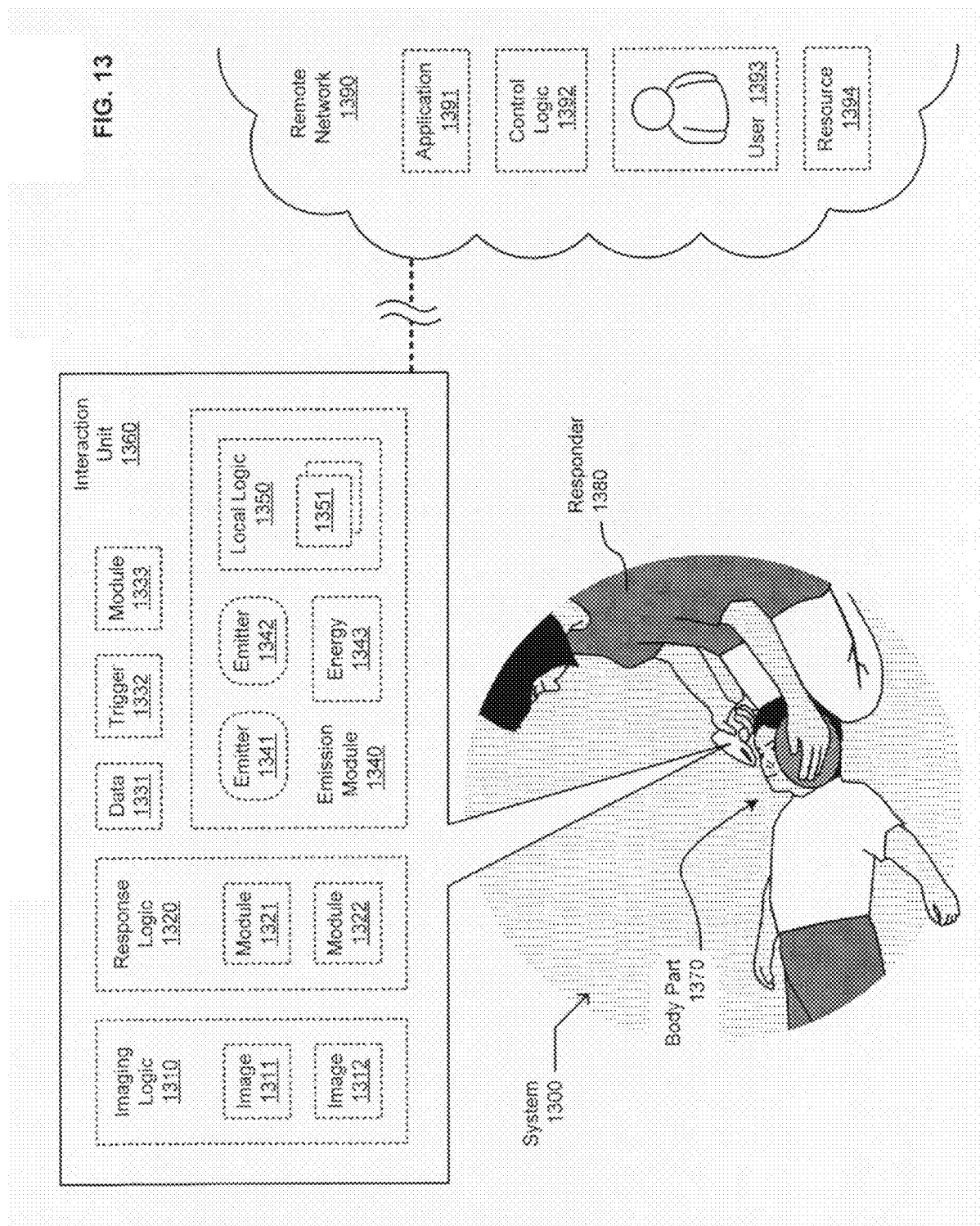

With reference now to FIG. 13 shown is a context in which one or more technologies may be implemented. System 1300 may comprise one or more instances of handheld or other interaction units 1360 having modules 1351 of local logic 1350 (for permitting a responder 1380 safely to trigger one or more emitters 1341, 1342, for example). Interaction unit 1360 may further comprise triggers 1332 or other user-operable controls, imaging logic 1310, response logic 1320, or other modules for permitting, causing, guiding, or otherwise facilitating the acquisition and processing of data 1331 according to a triage protocol or other protocol as described herein. In some contexts, for example, such devices may invoke linkages to one or more applications 1391, control logic 1392, emergency support experts or other users 1393, or other resources 1394 in remote networks 1390. Other such contexts are described above, for example, with reference to FIGS. 2-12.

An embodiment comprises (a) a finger trigger 1332 or other such emission control module operable for causing one or more emitters 1342 to emit x-rays and (b) a relay, software-controlled module 1333, or other such circuitry for resetting the emission control module partly based on a biometric or other certification of responder 1380 and partly based on an action by responder 1380. This can occur, for example, in a context in which module 1321 performs a fingerprint or voice certification, in which module 1322 responds to a trigger actuation, and in which the control module will not trigger an emission and/or will not be reset in response to an uncertified or unrecognized user's actions. In some contexts a preliminary x-ray emission (of less than 1 joule, e.g.) may be used for verifying an appropriate alignment with a target body part 1370, a wearable article, or some other article configured to detect and/or screen out a portion of the emitted energy 1343, for example, as a precursor to other operations as described herein. Alternatively or additionally, in some variants, such reset circuitry may be enabled responsive to such a certification and action by remote user 1393 facilitating a computed tomography scan or other emergency response protocol.

Another embodiment provides an interaction unit 1360 or other circuitry for transmitting an image 1311 of a body part 1370, in response to an action by a responder 1380 or other local entity, remotely to a specialty software application 1391 or other such entity. Some variants further comprise local logic 1350 configured to irradiate the body part 1370 (by activating emitter 1341 of emission module 1340, e.g.) and imaging logic 1310 or other imaging components configured to capture another image 1312 of the body part 1370 responsive to user 1393 or other remote resource 1394. This can occur, for example, in a context in which a subject would otherwise need to be taken to a remote facility for evaluation or in which a provider of interaction unit 1360 would otherwise need to staff and equip local radiology centers at substantial expense.

Figure 14:
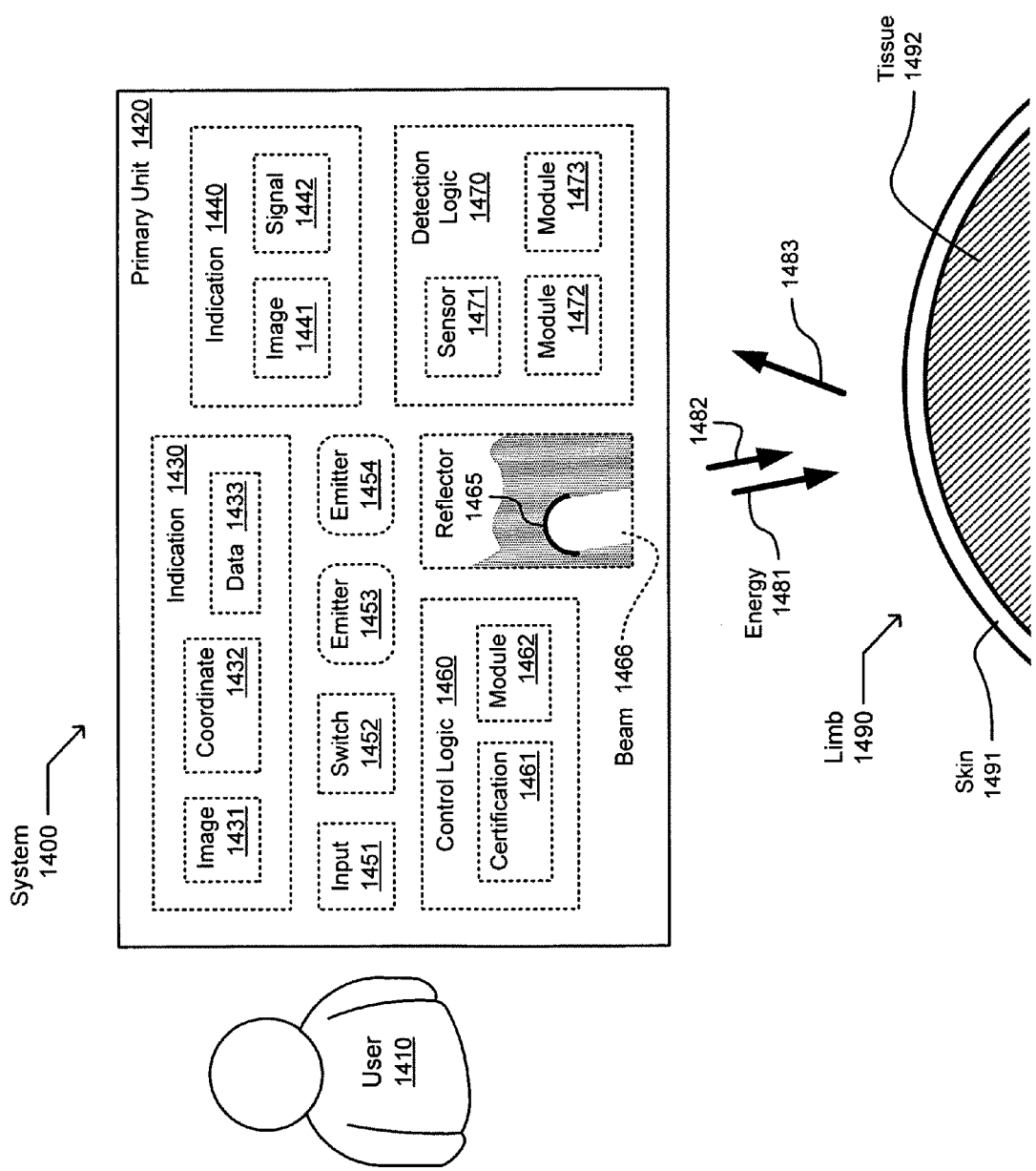

With reference now to FIG. 14 shown is a context in which one or more technologies may be implemented. System 1400 may comprise one or more instances of a primary unit 1420 positioned and/or activated by user 1410 and configured to emit energy 1482 (in a beam 1466 via reflector 1465, e.g.) toward a subject's limb 1490 or other body part. This can occur, for example, in a context in which user 1410 is not an imaging specialist and in which one or more modules 1473 of detection logic 1470 can image or otherwise detect a pressure ulcer, a tumor, or other pathologies manifesting in data 1433 from tissue 1492 beneath the subject's skin 1491. Alternatively or additionally, module 1473 can be tailored for more effective identification of pathologies for which delays in treatment greatly reduce its effectiveness. Other such contexts are described below, for example, with reference to FIGS. 16-22.

An embodiment provides an emission module (including at least emitter 1454, e.g.) operable for emitting (at least some) x-ray energy 1481; one or more sensors 1471 or other modules 1472 of detection logic 1470 (in a linear sensor array, e.g.) implementing circuitry for detecting an effect of x-ray energy 1481 or other energy 1482, through at least some tissue 1492 originating from the emission module. In some contexts, for example, the effect manifests as one or more images 1431, computed coordinates 1432, or other such indications 1430 as described herein. The embodiment may further include (a) one or more modules 1472 likewise configured to detect an effect of other energy 1483 (directly reflected or otherwise) from the body part and (b) one or more modules 1462 of control logic 1460 configured to reset the emission module partly based on a certification 1461 of a user 1410 and partly based on a vocal or other action (input 1451, e.g.) by the user. Such effects may include one or more images 1441, positional estimates, transitions in signals 1442, or other such indications 1440. Alternatively or additionally, such a reset operation may be implemented by software or other switches 1452 permitting a selective activation of one or more emitters 1453, 1454.

With reference now to FIG. 15 shown is a context in which one or more technologies may be implemented. System 1500 may comprise one or more instances of certification logic 1510 or other components of interface 1550 implement one or more data filters 1511, password protocols 1512, biometric authentication protocols 1513, skill verification protocols, or other such protocols 1514 effective for certifying a local or other user. In some variants, for example, such a certification may be guided via prompts at output 1541 and indicate or establish a relationship between the user(s) and a session 1521, function 1522, speaker or other such device 1523, service 1524, document 1525, or other such item 1526. Alternatively or additionally, one or more modules 1537 of decision logic 1535 may transmit a preference-indicative signal 1531 or other output signal 1532 remotely, for example, delegating or otherwise permitting "local" control (pursuant to user input 1542 and contingent upon a successful certification, e.g.). Many such interfaces may be used in systems described throughout this document.

With reference now to FIG. 16 shown is a context in which one or more technologies may be implemented. System 1600 may comprise one or more instances of a radiologist or other such certified user 1690 examining preliminary images 1682 in conjunction with symptoms, questions or other requests, or other contextual data 1681 relating to a pathology or circumstance. In some contexts, for example, user 1690 may respond (via a wireless linkage or network linkage 610, e.g.) with advice, a control parameter or signal, or other such guidance for facilitating (contemporaneously and/or remotely, e.g.) a subsequent acquisition of a refined primary image 1683 or other result data 1684 of a more specialized diagnostic utility. Other such contexts are described above, for example, with reference to FIGS. 6-14.

Figure 17:
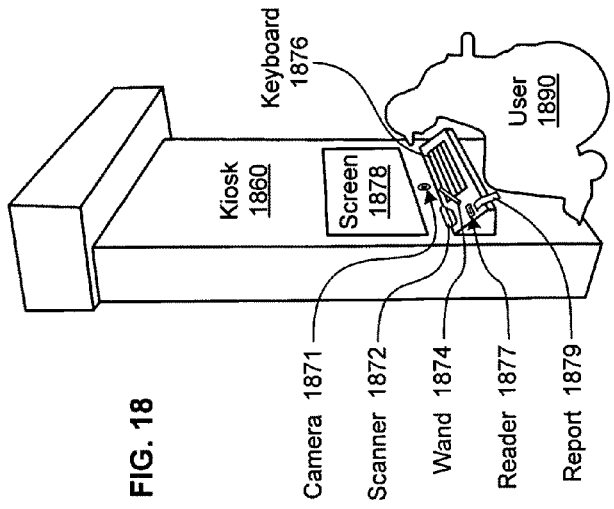

With reference now to FIG. 17 shown is a context in which one or more technologies may be implemented. Any of the above-described systems, for example, may include or interact with one or more modules 1731, 1732 of processing logic 1740 or modules 1722, 1723, 1724, 1725, 1726 of configuration logic 1720 as described herein. Such modules may update or act upon one or more apparent states 1752 (of an emission module 245, 340, 890, 1210 or other component, e.g.) or diagnoses 1753 (of a body part 325, 590, 1370 or subject or configuration, e.g.). Other such contexts are described below, moreover, with reference to FIGS. 18-22.

Many of the above-described embodiments may (optionally) include or interact with software-controlled or other modules for generating a scanned or other image in response to energy output from one or more emitters. See, e.g., U.S. Pat. No. 7,428,290 ("X-ray CT apparatus"); U.S. Pat. No. 7,423,933 ("Method for visualization of echoes received by an active sonar using a line spectrum emission"); U.S. Pat. No. 7,400,701 ("Backscatter inspection portal"); U.S. Pat. No. 7,386,150 ("Active subject imaging with body identification"); U.S. Pat. No. 7,339,603 ("Exposure device for an electrophotographic apparatus"); U.S. Pat. No. 7,218,704 ("X-ray backscatter mobile inspection van"); U.S. Pat. No. 6,977,375 ("Multi-beam multi-column electron beam inspection system"); U.S. Pat. No. 6,948,995 ("Manufacture method for electron-emitting device, electron source, light-emitting apparatus, and image forming apparatus"); U.S. Pat. No. 6,919,919 ("Light calibration device for use in low level light imaging systems"); U.S. Pat. No. 6,802,753 ("Method for manufacturing electron beam device, method for manufacturing image forming apparatus, electron beam device and image forming apparatus manufactured those manufacturing methods, method and apparatus for manufacturing electron source, and apparatus for manufacturing image forming apparatus"); U.S. Pat. No. 6,687,331 ("Method and device for making radiographic images"); U.S. Pat. No. 6,496,957 ("Design evaluating method and apparatus for assisting circuit-board assembly"); U.S. Pat. No. 6,449,337 ("X-ray computed tomography apparatus"); U.S. Pat. No. 6,359,651 ("Electronic camera using flash for exposure control"); U.S. Pat. No. 6,296,896 ("Manufacturing method for electron-emitting device, electron source, and image-forming apparatus"); U.S. Pat. No. 6,278,490 ("Exposure control for an image pickup apparatus that uses an electronic flash"); U.S. Pat. No. 6,246,463 ("Optical laser scanning device and image forming apparatus having the optical laser scanning device"); U.S. Pat. No. 6,094,472 ("X-ray backscatter imaging system including moving body tracking assembly"); U.S. Pat. No. 6,081,676 ("Electrophotographic image forming apparatus using guided light to detect waste toner in a process cartridge toner accommodating unit"). In light of teachings herein, for example, one or more of these techniques may be applied for implementing a module 1731 for computing an image 1751 in response to output 1756 resulting from a scanning or other emitter without undue experimentation. Other such embodiments are described, for example, with reference to FIGS. 2-5 & 19.

Such embodiments may likewise include circuitry for signaling whether one or more injuries or other physiological features are apparently recognizable in the digital image. In light of teachings herein, for example, numerous existing techniques may be applied for implementing software or other modules 1732 for extracting one or more pathology indicators 1757, user identifiers 1754, feature recognition protocols 1755, or other such indicators 1758 from or with a digital image without undue experimentation. See, e.g., U.S. Pat. No. 7,446,868 ("Micro defects in semi-conductors"); U.S. Pat. No. 7,437,025 ("Sensing system for detection and control of deposition on pendant tubes in recovery and power boilers"); U.S. Pat. No. 7,417,734 ("System and process for sorting biological particles"); U.S. Pat. No. 7,272,251 ("Method for detecting and classifying a structure of interest in medical images"); U.S. Pat. No. 7,242,817 ("System and method for detecting obstacle"); U.S. Pat. No. 7,126,699 ("Systems and methods for multi-dimensional metrology and/or inspection of a specimen"); U.S. Pat. No. 7,104,649 ("Wavefront characterization of corneas"); U.S. Pat. No. 7,034,740 ("Method and apparatus for identifying buried objects using ground penetrating radar"); U.S. Pat. No. 6,975,894 ("Digital topological analysis of trabecular bone MR images and prediction of osteoporosis fractures"); U.S. Pat. No. 6,831,664 ("Low cost interactive program control system and method"); U.S. Pat. No. 6,737,247 ("Imaging of enzymatic activity"); U.S. Pat. No. 6,652,461 ("Ultrasound device for three-dimensional imaging of internal structure of a body part"); U.S. Pat. No. 6,556,696 ("Method for segmenting medical images and detecting surface anomalies in anatomical structures"); U.S. Pat. No. 6,122,396 ("Method of and apparatus for automating detection of microorganisms"). Other such embodiments are described below, for example, with reference to FIGS. 19-22.

Some of the above-described embodiments may (optionally) interact with a special-purpose linkage or other circuitry for resetting the one or more activation-history-dependent features in response to an authorization from a certified service provider or other user. In light of teachings herein, for example, numerous existing techniques may be applied for implementing one or more modules 1722 of configuration logic 1720 for initializing one or more operational indicators 1715 or otherwise contingently resetting one or more logic modules (of control logic 140, 360, 640, 830, 1392, e.g.) without undue experimentation. See, e.g., U.S. Pat. No. 7,436,291 ("Protection of devices in a redundant configuration"); U.S. Pat. No. 7,411,766 ("Circuit interrupting device with end of life testing functions"); U.S. Pat. No. 7,266,988 ("Resettable latching MEMS shock sensor apparatus and method"); U.S. Pat. No. 7,239,064 ("Resettable latching MEMS temperature sensor apparatus and method"); U.S. Pat. No. 7,085,805 ("Remote device management in grouped server environment"); U.S. Pat. No. 6,658,597 ("Method and apparatus for automatic recovery of microprocessors/microcontrollers during electromagnetic compatibility (EMC) testing"); U.S. Pat. No. 6,617,963 ("Event-recording devices with identification codes"); U.S. Pat. No. 6,584,587 ("Watchdog method and apparatus"); U.S. Pat. No. 6,460,093 ("Automatic configuration of primary and secondary peripheral devices for a computer"); U.S. Pat. No. 6,259,358 ("School bus safety device"). Some variants of processing unit 1700 may, for example, comprise configuration logic 1720 or other circuitry for generating, requesting, or acting upon one or more thresholds 1711, 1712, scores 1713 or other computed quantifications 1716, results 1717, or other such determinants 1718 as described herein. Other such contexts are described above, for example, with reference to FIGS. 8-14.

Some of the above-described embodiments may include or otherwise interact with one or more software modules 1726 or other circuitry for triggering a determination of whether an organ or other physiological feature is apparently recognizable in image 1751. In some contexts, for example, module 1725 may obtain such result 1717 by transmitting digital image to a remote specialist or other such evaluation resource.

Alternatively or additionally, many of the above-described embodiments may comprise special-purpose circuitry for deciding whether to disable or alter an emission level of an emission module in response to a comparison between one or more parameters of an emission and a reference value. Such decisions can occur, for example, in a context in which one or more modules 1724, 1725 of configuration logic 1720 implement a user-specified protocol in which an emission module will be disabled whenever an emitter thereof apparently (a) is fired for the Nth time and/or (b) emits a total of at least X joules and/or (c) emits a pulse of more than $10^{10}$ photons or longer than 80 milliseconds (as threshold 1711, e.g.) and/or (d) crosses some other such threshold 1712. See, e.g., U.S. Pat. No. 7,432,667 ("Projector lamp control for increased lamp life"); U.S. Pat. No. 7,423,688 ("Lighting control apparatus"); U.S. Pat. No. 7,397,202 ("Brightness control circuit and backlight control module"); U.S. Pat. No. 7,321,348 ("OLED display with aging compensation"); U.S. Pat. No. 7,301,868 ("Optical disk recording/reproducing method and recording/reproducing apparatus using the same"); U.S. Pat. No. 7,276,681 ("On-board light source based gain correction for semi-active laser seekers"); U.S. Pat. No. 7,116,471 ("Method and system for improved eye protection safety of distributed Raman amplifiers"); U.S. Pat. No. 6,870,521 ("Method and device for driving plasma display panel"); U.S. Pat. No. 6,423,963 ("Safety latch for Raman amplifiers").

Other such embodiments are described above, for example, with reference to FIGS. 1-3 & 8.

Figure 18:
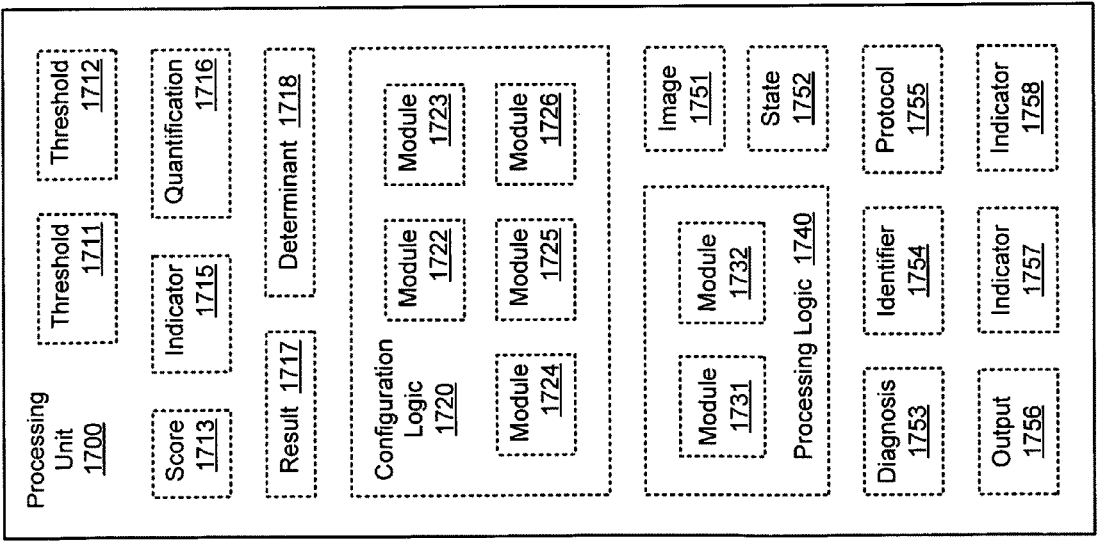

With reference now to FIG. 18 shown is a context in which one or more technologies may be implemented, a kiosk 1860 permitting a pedestrian or other unspecified user 1890 to perform medical imaging or other diagnostic functions remotely (in a resort, fuel station, or elder care facility, for example, far from a hospital or laboratory). Kiosk 1860 may include one or more instances of visible-spectrum cameras 1871, handheld scanners 1872 or wands 1874, microphones or other data entry devices (keyboard 1876, e.g.), card readers 1877 or data ports (for reading intake forms, payment data, medical histories, or other such data from a magnetic card, printout, or other portable data-handling medium, e.g.), or output devices (screens 1878 or printers for presenting reports 1879 or other results, e.g.). Such stations may be configured for use (at a point-of-care station accessible to a driver or other user 1890, for example) with any of the above-described systems.

Figure 19:
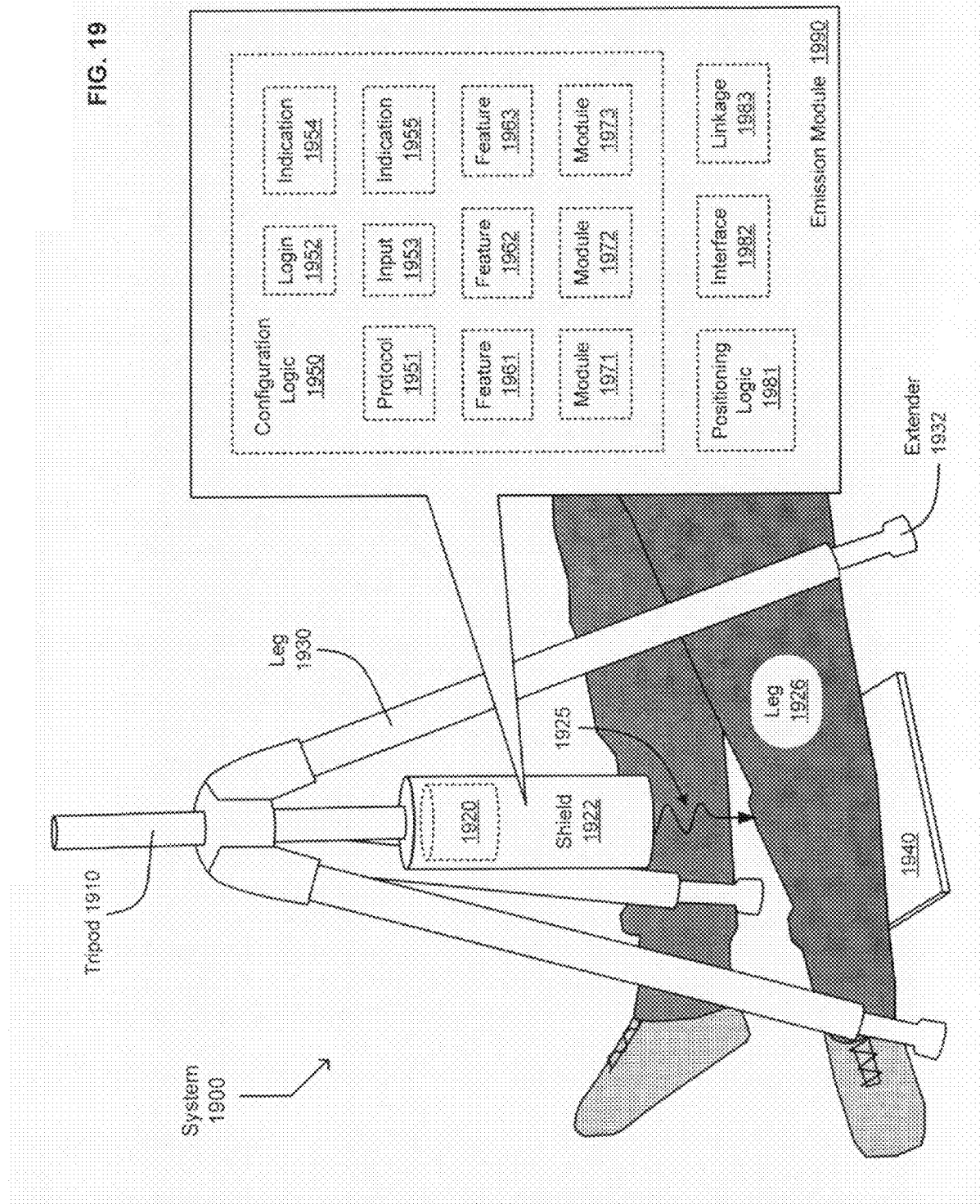

With reference now to FIG. 19 shown is a context in which one or more technologies may be implemented. System 1900 may comprise one or more instances of a support (legs 1930 or tripod 1910, e.g.) configured to position an energy emitter 1920 in relation to a shield 1922, a body part or other target, and/or a plate 1940 or other energy detection apparatus. In some variants, for example, emission module 1990 may include (a) one or more modules 1973 for controlling one or more emitters 1920 as described above and/or (b) positioning logic 1981 operable for controlling extenders 1932 or other components of the support, for example, in response to preliminary images or commands from a remote user 220, 1393. Other such contexts are described above, for example, with reference to FIGS. 2-8 & 16-18.

An embodiment provides a system comprising one or more safety features 1961 or other activation-history-dependent features 1962 configured to prevent an inexperienced user from being able to release more than a maximum (on the order of 30 or 100 joules, e.g.) of ionizing radiation or other potentially dangerous energy 1925 into a body part (leg 1926, e.g.) via the emission module 1990. In some variants, for example, one or more modules 1971 of configuration logic 1950 may include circuitry for maintaining an emission module 340, 890, 1210, 1990 in a disabled state until a certifiable user is present or in real-time communication with a local responder 380. Such certification may arise from one or more of a recognizable login 1952, a responder's successful tutorial or other on-site demonstration of knowledge or skill, an indication 1954 that a real-time guidance protocol 1951 is warranted, or in other such circumstances as described above (with reference to FIGS. 2-8, e.g.).

Another embodiment comprises an emission module 1990 operable for emitting energy 1925 through air, one or more sensing elements (an exposure area of plate 1940 or other detection units, e.g.) configured to receive a portion of the energy 1925 through a leg 1926 or other body part from the emission module 1990. The embodiment may further comprise one or more modules 1972 for resetting the emission module 1990 at least partly based on a vocal input 1953 or other indication 1955 of an action by a certified user. This may occur, for example, in a context in which emission module 1990 includes (a) control logic or other local features 1963 as described above or (b) a local user interface 1982 or other linkage 1983 with a user group or other remote resource as described herein.

In light of teachings herein, numerous existing techniques may be applied for configuring a shield for ionizing radiation, an emitter configuration, a reflector, a support, or other such structures to facilitate selective exposure of detectors and other targets as described herein without undue experimentation. See, e.g., U.S. Pat. No. 7,375,358 ("Radiation shield for portable x-ray fluorescence instruments"); U.S. Pat. No. 7,356,123 ("X-ray device having a collimator, and method of setting the latter"); U.S. Pat. No. 7,315,607 ("Mammograph system with a face shield"); U.S. Pat. No. 7,289,603 ("Shield structure and focal spot control assembly for x-ray device"); U.S. Pat. No. 7,220,256 ("Laser system and method for treatment of biological tissues"); U.S. Pat. No. 7,211,814 "Standoff radiation attenuation system"); U.S. Pat. No. 7,188,625 ("Ocular surgical protective shield"); U.S. Pat. No. 7,109,505 ("Shaped biocompatible radiation shield and method for making same"); U.S. Pat. No. 7,071,692 ("Radio frequency shield for nuclear magnetic resonance procedures"); U.S. Pat. No. 6,965,118 ("Radiation shield for portable x-ray fluorescence instruments"); U.S. Pat. No. 6,910,999 ("Miniature x-ray unit"); U.S. Pat. No. 6,869,427 ("LED fixation device for topical anesthesia eye surgery"); U.S. Pat. No. 6,779,920 ("X-ray localizer light system"); U.S. Pat. No. 6,768,925 ("Method for improved safety in externally focused microwave thermotherapy for treating breast cancer"); U.S. Pat. No. 6,681,771 ("Organ shields for medical procedures"); U.S. Pat. No. 6,618,465 ("X-ray shielding system and shielded digital radiographic inspection system and method"); U.S. Pat. No. 6,549,609 ("X-ray generator with a limiting device"); U.S. Pat. No. 6,320,938 ("Method of X-ray protection during diagnostic CT imaging").

Figure 20:
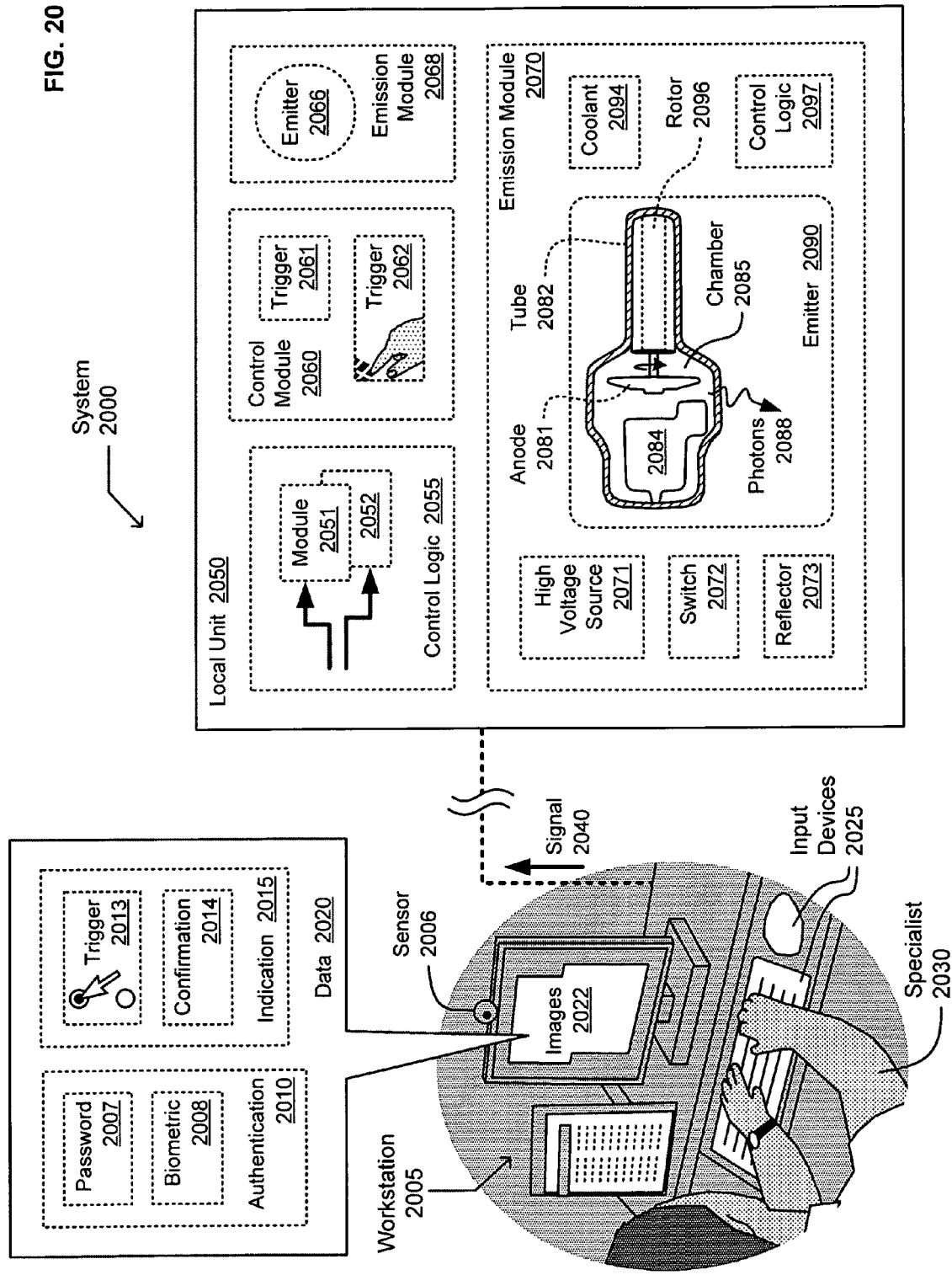

With reference now to FIG. 20 shown is a context in which one or more technologies may be implemented. System 2000 may comprise one or more instances of a workstation 2005 for use by a specialist 2030 remote from a local unit 2050 comprising one or more emission modules 2068, 2070 each comprising one or more emitters 2066, 2090. In some contexts, such an emitter may include one or more anodes 2081 in a vacuum chamber 2085 (of tube 2082, e.g.) containing a cathode 2084. When control logic 2097 causes switch 2072 to couple high voltage source 2071 across anode 2081 and cathode 2084, electrons from cathode 2084 collide with anode 2081 to produce photons 2088. In some contexts, an operating life of emitter 2090 may be greatly extended by causing anode 2081 to rotate on rotor 2096, for example, or to keep anode 2081 from significant charring by applying an appropriate flow of coolant 2094 outside chamber 2085. Alternatively or additionally, such photons may be spread, concentrated, or otherwise directed (by one or more reflectors 2073 or lenses, e.g.) in any of several existing configurations. In some variants, moreover, local unit 2050 may include one or more modules 2051, 2052 of control logic 2055, such as for implementing various components of processing units 1700 or communications functions as described herein.

Alternatively or additionally, system 2000 may include one or more sensors 2006 or input devices 2025 for use by specialist 2005. Some variants may include (a) one or more emission modules 2068, 2070 operable for emitting photons 2088 or other energy into a subject's body part, (b) one or modules 2051 configuring circuitry for detecting an effect of the other energy upon the body part, (c) circuitry for detecting an effect of the photons 2088 upon the body part, and (d) one or more modules 2052 configuring circuitry for resetting the emission module(s). This can occur, for example, in a context in which such control logic 2055 responds to a signal 2040 indicating an authentication 2010 or other certification of a user (responsive to a password 2007 or biometric 2008, e.g.) and an action by the user. A remote specialist 2030 may take such actions via trigger 2013, confirmation 2014, indication 2015, or other such data 2020, for example, optionally in response to one or more images 2022 presenting data from local unit 2050.

In some contexts, for example, such modes of control permit a specialist or other personnel to operate, reset, or otherwise configure local unit 2050 without having to travel to a facility containing local unit 2050. Alternatively or additionally, one or more control modules 2060 may include remote or other triggers 2013, 2061, 2062 operable for activating an x-ray emitter 2090 or other emitter 2066, as well as control logic 2055 or other circuitry for resetting the control module(s) 2060 partly based on an identity authentication 2010 or other certification of a remote specialist 2030 or other user and partly based on a signal 2040 indicative of an action by such user(s). Other such contexts are described above, for example, with reference to FIGS. 2-14.

Figure 21:
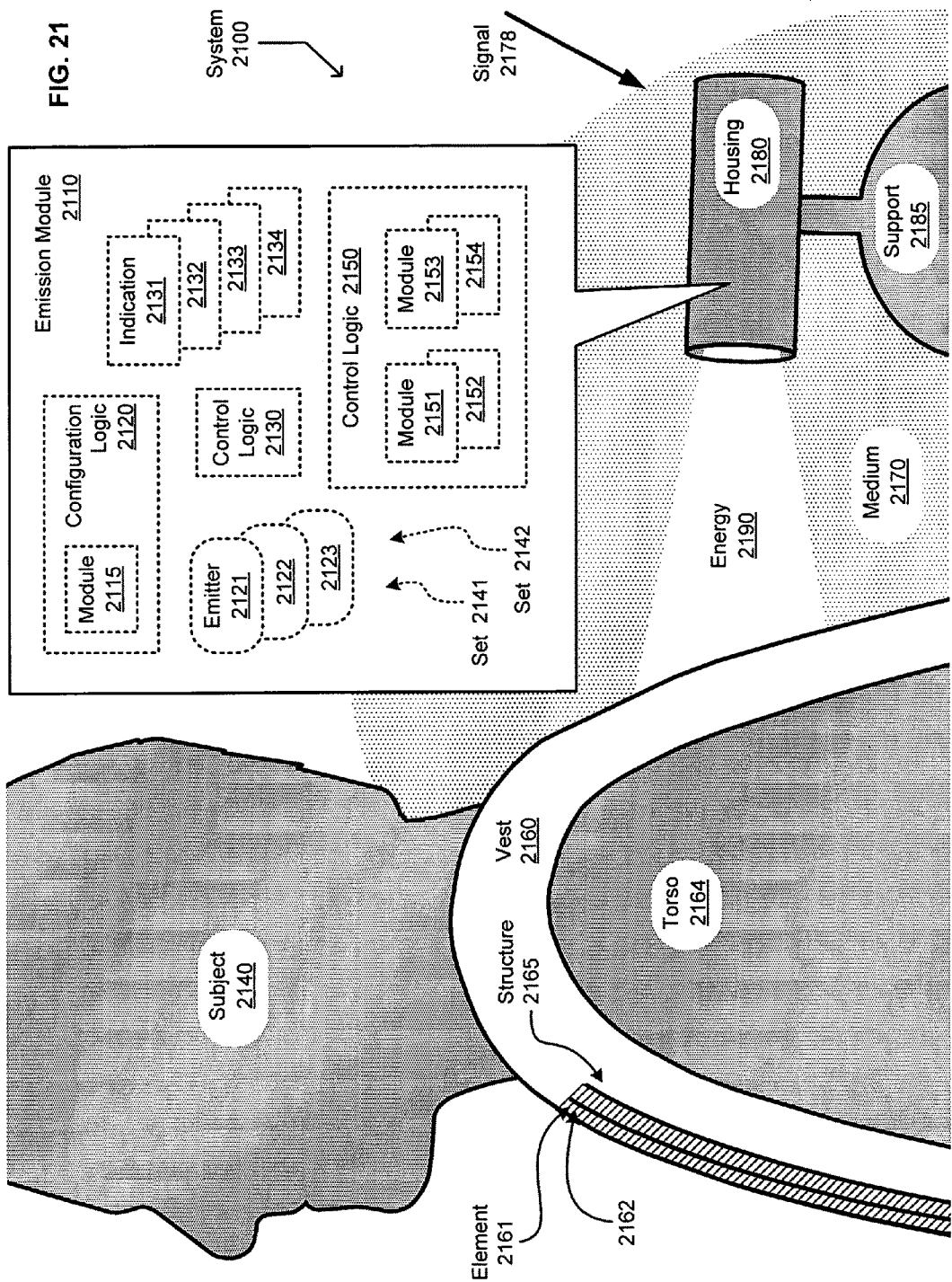

With reference now to FIG. 21 shown is a context in which one or more technologies may be implemented. System 2100 may comprise one or more instances of an emission module 2110 in a housing 2180 (optionally on a tripod or other support 2185, e.g.) operable for transmitting energy 2190 through a wireless medium 2170. An embodiment provides (a) an ionizing radiation control module or other emission module 2110 and (b) a reset module 2115 or other circuitry for resetting or otherwise configuring the emission module 2110 locally in response to a remote signal 2178. This can occur, for example, in a context in which emission module 2110 is operable (for biological imaging or therapeutic treatments, e.g.) locally in response to a timer activation, a wireless controller activation, or some other direct response to an action by subject 2140.

Another embodiment comprises (a) emission module 2110 comprising circuitry for emitting energy 2190 and (b) a vest 2160, shoe, helmet, or other wearable article configured to support two or more sensing elements 2161, 2162 each in a position suitable to receive a portion of the energy 2190 (for imaging through torso 2164 or other body part, e.g.) from the emission module 2110. This can occur, for example, in a context in which emission module 2110 includes or otherwise interacts with control logic 2130 and one or more emitters 2121, 2122, 2123 operable for emitting energy 2190 suitable for imaging through the body part. In some variants, the embodiment may further include a reset module 2115 (of configuration logic 2120) for resetting at least some control logic 2130 of the emission module 2110 partly based on a type or other indication 2131 of a user action (by a remote user, for example, via signal 2178) and partly based on (an indication 2132 of) a certification of the user.

Yet another embodiment provides (a) first and second overlapping sets 2141, 2142 of energy emitters 2121, 2122, 2123; (b) an image detection structure 2165; (c) one or more modules 2151 of control logic 2150 or other circuitry for causing a use of the first energy emitter set 2141 and (indirectly) of the image detection structure 2165; and (d) one or more modules 2152 of control logic 2150 for causing a use of the second energy emitter set 2142 and of at least the image detection structure 2165. This can occur, for example, in a context in which one or more users have been certified (as competent or authorized, e.g.) before or after providing input 387, 1542 invoking control logic 2130 to activate the second energy emitter set 2142.

In some variants, emission module 2110 may include or otherwise interact with reset module 2153 (of control logic 2150, e.g.) configured as software-controlled or other circuitry for disabling control logic 2130 in response to one or more indications 2133 that the wearable article is not being worn or is being worn improperly. Alternatively or additionally, emission module 2110 may interact with another such reset module 2154 configured as software-controlled or other circuitry for enabling control logic 2130 in response to one or more indications 2134 that the wearable article(s) and emission module 2110 have proper relative alignment.

Figure 22:
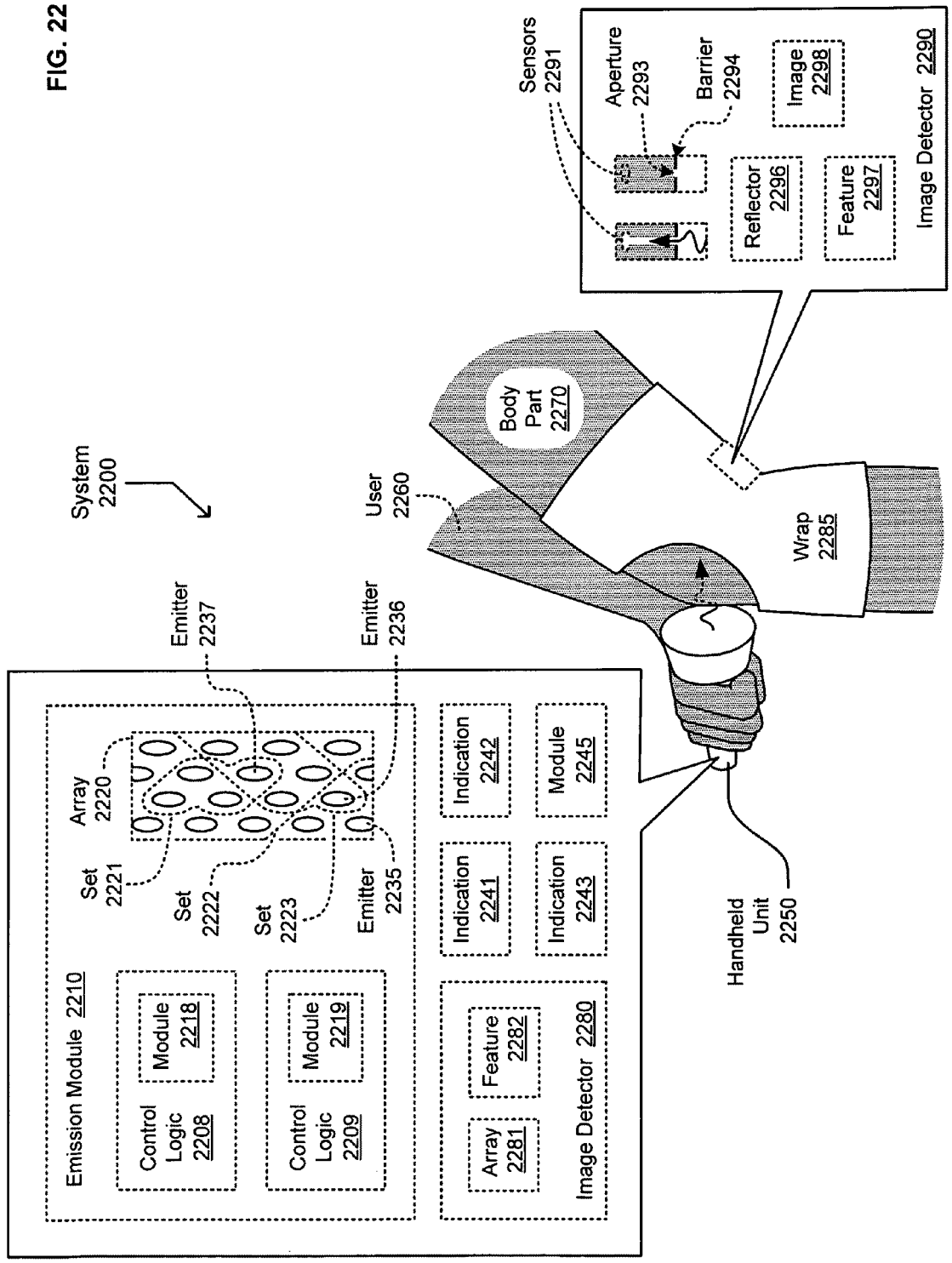

With reference now to FIG. 22 shown is a context in which one or more technologies may be implemented. System 2200 may include one or more arrays 2220 or other sets 2221, 2222 of emitters 2237 (in or controlled by emission modules 2210 as described herein, e.g.) configured to transmit energy (manipulable by barriers 2294, gratings, linear arrays, reflectors 2296, or other such features, e.g.) suitable for forming an image 2298 in an image detector 2290 as described herein. Other such contexts are described above with reference to various systems.

An embodiment provides one or more modules 2218 of control logic 2208 for causing a use of a set 2222 of one or more energy emitters 2235, 2236 and of one or more arrays 2281, sensors 2291, apertures 2293, or other features 2282, 2297 of an image detector 2280, 2290. The embodiment further provides one or more modules 2219 of control logic 2209 for causing a use of a superset or other overlapping set 2223 of energy emitters 2236, 2237 and of at least one feature 2282, 2297 (in response to various indications 2241-2243 as described below, e.g.). This can occur in a context in which user 2260 is authorized to activate handheld unit 2250, for example, for scanning a body part 2270 (of another individual, e.g.). In some variants, for example, module 2245 may be configured to generate such a recognition or other such positive indication 2241 responsive to (a) detecting a fingerprint, voiceprint, or other such raw indication 2242 (successfully certifying user 2260, e.g.) and to (b) detecting a subsequent or other button press, verbal command, or other preference-indicative action (as indication 2243, e.g.). Alternatively or additionally, module 2245 may be configured to transmit energizing radiation only upon confirming an appropriate position of handheld unit 2250 (relative to a wrap 2285 or other such article, e.g.). In some contexts, moreover, an image detector 2290 or wrap 2285 may comprise a shield or other such feature 2297 (effective for blocking a majority of an ionizing radiation directed toward a body part, for example, such as by limiting intensity, exposure time, or other such dosage control parameters).

With reference now to FIG. 23, shown is a flow 2300 that may be performed in one or more of the above-described contexts. Flow 2300 may include one or more instances of operation 2330—obtaining an indication of one or more attributes of an emission module (e.g. one or more instances of configuration logic 1265, 1720, 1950 obtaining such indications 1955 as a priori knowledge or by interaction with a user or local unit 250, 650, 2050). This can occur, for example, in a context in which an above-described embodiment includes or interacts with such configuration logic, optionally under the control of a specialist 2030 or other remote entity. In some variants, moreover, operation 2330 may include one or more instances of these operations: 2332, 2335, or 2337.

Operation 2332 describes sensing a position of the emission module relative to a stationary article (e.g. one or more modules 1723 determining whether one or more images 1751 from a wand 1874 or other handheld instrument depicts a landscape, a kiosk 1860 or other artificial structure, or other such recognizable features indicating whether the instrument is appropriately positioned relative to a stationary subject). This can occur, for example, in a context in which the instrument contains or conveys energy from the emission module, in which precise positioning is critical for effective measurement, and in which a user 1890 may take an unknown amount of time to position the instrument and subject. Alternatively or additionally, one or more proximity detectors, sensors in wearable articles, remote users 220 or other specialized resources, or other modes of detection (as described above with reference to FIGS. 1-22, e.g.) can be used for confirming positional suitability.

Operation 2335 describes sensing a position of the emission module relative to one or more of a wearable article or a body part (e.g. module 1725 receiving coordinates, preliminary images, or other indications that a leg 1926, vest 2160, wrap 2285, or other part of or article worn by a subject 2140 is appropriately positioned for effective diagnostic imaging of a target body part 1370). This can occur, for example, in a context in which a guidance unit 1000 includes or interacts with configuration logic 1265, 1720, 1950, 2120 and in which in which module 1725 receives raw, real-time data indicative of such positioning from a camera 1871 or other stationary sensor, a scanner 1872 or other handheld sensor, or some other such detection circuitry as described herein. In some variants, for example, module 1725 may guide a user 1080, 1890 verbally through a sequence 1081 of positioning operations. Alternatively or additionally, module 1725 may effectively confirm that such wearable articles position sensing elements in suitable positions for irradiating a target region of interest, especially in contexts in which the emissions might otherwise expose other body parts to irradiation unnecessarily. See, e.g., FIG. 2, 3, 12, 21, or 22.

Operation 2337 describes sensing a type of the emission module (e.g. module 1723 detecting a model or component identifier, a frequency range or other emission type, or other such static parameters of an emitter or its mode of operation). This can occur, for example, in a context in which module 1723 communicates with one or more modules 222 of control logic 140, 295, 640 920; detection logic 1150, 1240, 1470; or other components having an indication of an emission or emission module type. (In some embodiments, a frequency range or other "type" of an irradiation, operating mode, emission module, or other such entity may refer to an entirety of its energy or to a majority or other substantial component thereof. As exemplified herein, many such entities may thus belong to two or more "types.") In some variants, for example, module 1723 may use such information for adapting an imaging or other irradiation, for annotating data arising from the irradiation, or for invoking one or more special protocols 1092 to ensure safe and effective emission module operation.

Flow 2300 may further include one or more instances of operation 2360—invoking circuitry for causing an irradiation in response to the indication of the one or more attributes of the emission module (e.g. one or more instances of control logic 225, 295 or other response logic enabling or triggering an imaging or other irradiation in response to a type or other attribute of an emission module 245, 340, 890, 1210, 1990). This can occur, for example, in a context in which one or more protocols 1091, 1238, 1514, 1755, 1951 described herein are implemented in software, in which an emission is contingent upon a "ready" state of the emission module, and in which any positioning or other preconditions imposed by the protocol(s) are met. In some variants, for example, operation 2360 may include one or more instances of these operations: 2361, 2363, 2366, or 2368.

Operation 2361 describes triggering an emission of visible light partly based on a user action and partly based on at least one of the one or more attributes of the emission module, as the irradiation (e.g. one or more modules 222, 223 of control logic causing one or more emitters 262, 263 to emit at least some visible light as energy 283). This can occur, for example, in a context in which energy 283 combines two or more types of energy emissions. In some variants, for example, an X-ray or other emitter emits other types of energy simultaneously or in alternation to signal the activation and other attributes of the X-ray component. Alternatively or additionally, one or more preliminary emissions may be used for verifying positional suitability or for other tasks as described above. Such emission operations may likewise incorporate or interact one or more instances of sterilization, therapeutic applications, or other modes of irradiation as described herein.

Operation 2363 describes receiving one or more results of the irradiation via a wearable article (e.g. one or more modules 1236 of detection logic 1240 receiving therapeutically relevant signals 1531 or other detectable energy 1225 in or from a patch 1251, wrap 2285, or other wearable article 1254). This can occur, for example, in a context in which the article(s) contain or interact with configuration logic 1265, 1720 that performs operation 2330, and in which detection logic 1240 and one or more emission modules 1210 jointly perform operation 2360. Alternatively or additionally, in some contexts, remote evaluation logic 210 or users 220 may receive diagnostic data via such articles.

Operation 2366 describes enabling the circuitry for causing the irradiation in response to a remote signal (e.g. one or more modules 363, 1462 of control logic resetting or otherwise enabling one or more emitters 1453 or other emission modules 245 in response to a remote instance of signal 609, 1442). This can occur, for example, in a context in which a local unit 250, 650 has a wireless or other network connection and in which some remote source transmits the signal 370 to a wireless interface or other local receiver. In some variants, for example, a remote entity may generate such an enabling signal only when one or more conditions are met: that prior emissions via the local unit were performed satisfactorily or adequately explained, that a next irradiation or diagnostic has been paid for, that a local unit is apparently well-positioned for irradiating a target region, or other such conditions as described above. Alternatively or additionally, such a condition may be confirmed locally, in some protocols, before or after such an authorization by the remote entity.

Operation 2368 describes enabling the circuitry for causing the irradiation in response to a user certification (e.g. module 1321 triggering an enablement of or emission from emission module 1340 in response to a password entry or other such action by a responder 1380 or other user 1393). This can occur, for example, in a context in which module 1321 prompts responder 1380 for such a certification (of competence or authority, for example) before or after responder 1380 tries to trigger an emission. In some variants, for example, local logic 1350 may request such an input in response to an indication that responder 1380 is trying to cause emission module 1340 to emit ionizing radiation (as contrasted with infrared or other modes of emission, for example, that may available). Alternatively or additionally, in some variants, a more-specialized user 1393 may (optionally) be called to participate in authorizing some emissions (a sterilizing emission of 5 to 20 kilojoules or more, e.g.). Such interaction units 1360 or other handheld devices may likewise incorporate or interact one or more instances of preliminary imaging or verbal interface protocols, for example, to confirm the appropriateness of a proposed emission.

With reference now to FIG. 24, shown is a flow 2400 that may be performed in one or more of the above-described contexts. Flow 2400 may include one or more instances of operation 2420—obtaining an indication of a user action (e.g.

one or more instances of local units 2050 or other detection components signaling an input, positioning action, or other detectable condition warranting an irradiation). This can occur, for example, in a context in which a user has been or might be certified for triggering, resetting, or otherwise facilitating an irradiation as described above. In some variants, moreover, operation 2420 may include one or more instances of these operations: 2423, 2426, or 2427.

Operation 2423 describes obtaining an evaluation of an apparent positional suitability of an emission module relative to one or more sensing elements (e.g. one or more modules 1235, 1236 of detection logic evaluating whether emission module 1210 is positioned to emit energy 1225 toward sensors 1233). This can occur, for example, in a context in which such a module obtains a measurement 1249 of a preliminary portion of such energy 1225, in which such a module detects an unpowered source unit (via another emission module 1255, e.g.), or in which interface 1218 effectively signals such apparent suitability responsive to input from user 1230. In some variants, for example, detection logic 1240 may signal an apparent positional suitability only in response to two such indications. Alternatively or additionally, one or more such modules may detect or otherwise work in conjunction with a wearable article 1254 configured to support one or more sensors 1233 operable to receive a portion of the energy 1225 through a body part from the emission module 1210.

Operation 2426 describes receiving the indication from a user who has received a preliminary image (e.g. keyboard 1876 accepting a "capture image" menu selection from user 1890 after screen 1878 displays some indication of a view from a scanner 1872 or wand 1874). This can occur, for example, in a context in which a user 240 has access to a public kiosk, in which kiosk 1860 comprises an instance of a local unit 250 implementing interface 1550, in which control logic 295 and keyboard 1876 jointly perform operation 2420, and in which protocol 1514 directs such output to screen 1878 to ensure that one or more emitters 262 are properly positioned. In some variants, for example, such control logic may then perform operation 2470 (jointly with emission module 245, e.g.) by triggering the irradiation (via an emitter 262 in scanner 1872, e.g.). Alternatively or additionally, one or more remote users 220 may likewise perform operation 2426 in cooperation with local facilities or users.

Operation 2427 describes providing guidance to facilitate the user action (e.g. a handheld unit 790 displaying one or more reference symbols 761 and subject symbols 762 in a common image 760 to specify a desirable range or motion). This can occur, for example, in a context in which local unit 2050 implements such a handheld unit 790, a conic section or other reference symbol 761 denotes a target range of positions for unit 790, in which another conic section or other subject symbol 762 denotes a current position of unit 790 relative to the desirable range, and in which a user 780 may change at least the relative positions of such symbols (effectively in real time, e.g.) by moving unit 790 manually. In some variants, for example, a specialist 2030 or other such resource may provide suitable data (by moving a handheld counterpart unit or other such input device 2025 in real time, e.g.) defining a target range. Alternatively or additionally, a local help feature or other such guidance may likewise indicate how user 780 can best position unit 790 relative to a region 770 of interest.

Flow 2400 may further include one or more instances of operation 2470—invoking circuitry for causing an irradiation of at least a part of a subject's body in response to the indication of the user action (e.g. one or more instances of control logic 225, 295, processing logic 1740, or other response logic enabling or triggering an imaging or other irradiation in response to a type or other attribute of an emission module 245, 340, 890, 1210, 1990). This can occur, for example, in a context in which the user action (locally or otherwise) signals an apparent readiness for the irradiation and in which one or more participating users have certified as described herein. In some variants, for example, operation 2470 may include one or more instances of these operations: 2472, 2475, or 2479.

Operation 2472 describes transmitting a digital image of a body part resulting from an activation of an emission module (e.g. one or more modules 930 transmitting one or more facial images 931 and/or diagnostic images 936 facilitated by a flash or other emission as described herein). This can occur, for example, in a context in which such images are immediately or subsequently received by a care provider. In some variants, for example, medical history data or other such contextual indications 935 may accompany the transmission to facilitate a recipient's evaluation.

Operation 2475 describes detecting an effect of the irradiation of the part of the subject's body (e.g. module 1732 detecting one or more instances of images 1751, measurements, diagnoses 1753, or other such data resulting directly or indirectly from energy irradiating a body part as described herein). This can occur, for example, in a context in which absorbed or reflected portions of the energy are detected directly, in which such measurements or other processed data may be derived immediately from such detections, and in which a certified or other user effectively controls an emission module remotely through a wireless medium (such as by cellular, 802.11b/g/n, wireless USB, or radio linkages). Alternatively or additionally, module 1732 may be configured (jointly with invocation logic 960, e.g.) to relate such detections with opinion data or other such distillations in due course, such as by soliciting a response in forwarding the detected data immediately to an expert or other human participant.

Operation 2479 describes causing one or more sensing elements to receive a portion of energy resulting from the irradiation (e.g. one or more modules 961 invoking control logic 920 or other circuitry operable for triggering an emission as described herein). This can occur, for example, in a context in which one or more emission modules 1210, 1340, 1990, 2068, 2110 include or otherwise interact with utility unit 900, in which (at least) invocation logic 960 performs operation 2470, and in which one or more sensors 1171, 1233, 1471, 2291 are positioned to detect the energy portion (reflected off or transmitted through a body part of interest, e.g.). In some variants, moreover, one or more of such emission modules may implement activation-history-dependent features 882, certification protocols, or other such safety features as described herein.

Some or all of the embodiments described herein may generally comprise technologies for handling one or more bioactive agents and/or carriers in releasable module form, via a liquid-bearing conduit, in a mist or other spray form, in a pumped or other pressurized form, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/of electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a"

and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Various aspects of the subject matter described herein are set out in the following numbered clauses:

What is claimed is:

1. A system comprising:
   means for emitting energy through a wireless medium;
   means for detecting an action by a user and for emitting a sensor signal responsive to a detected action by the user;
   means for receiving user input;
   means for certifying the user at least partly responsive to received user input, wherein the means for certifying the user certifies the user by at least one of authenticating an identity of the user or verifying that the user is qualified to use the means for emitting;
   means for outputting a certification signal responsive to the user certification;
   means for resetting the means for emitting energy partly based on the sensor signal and partly based on the certification signal; and
   means for positioning one or more sensing elements to receive a portion of the energy from the means for emitting energy, the means for positioning including a wearable article that is an article of clothing.

2. A system comprising:
   an emission module operable for emitting energy through a wireless medium;
   circuitry for detecting an action by a user;
   circuitry for emitting a sensor signal responsive to a detected action by the user;
   circuitry for receiving user input;
   circuitry for certifying the user at least partly responsive to received user input, wherein the circuitry for certifying the user is configured to certify the user by at least one of authenticating an identity of the user or verifying that the user is qualified to use the emission module;
   circuitry for outputting a certification signal responsive to the user certification;
   circuitry for resetting the emission module partly based on the sensor signal and partly based on the certification signal;
   one or more sensing elements for receiving a portion of the energy through a body part from the emission module; and
   a wearable article configured to support the one or more sensing elements to receive the portion of the energy through the body part from the emission module, the wearable article being an article of clothing.

3. The system of claim 2, further comprising:
   a display configured to present video data in a vicinity of the emission module.

4. The system of claim 2, further comprising:
   a display configured to present a facial image in a vicinity of the emission module.

5. The system of claim 2, further comprising:
a speaker configured to present audio data in a vicinity of the emission module.

6. The system of claim 2, further comprising:
an interface that includes at least one user input device; and
a kiosk supporting the emission module, the circuitry for detecting an action by the user, the circuitry for certifying the user, and the interface.

7. The system of claim 2, further comprising:
an interface configured to present data in response to a received second sensor signal emitted by the circuitry for emitting based on a detection of another action by the user.

8. The system of claim 2 in which the emission module comprises:
an ionizing radiation emission module operable for emitting ionizing radiation energy;
circuitry for detecting an emission from the ionizing radiation emission module and for measuring or for determining cumulative emissions of the ionizing radiation emission module and for emitting an emissions signal responsive to the measured or determined cumulative emissions; and
circuitry for preventing excessive cumulative emissions by responding to the emissions signal by preventing activation of the ionizing radiation emission module if further activation of the ionizing radiation emission module would permit the user to release more than a threshold of ionizing radiation energy via the ionizing radiation emission module.

9. The system of claim 2 in which the emission module comprises:
an ionizing radiation emission module operable for emitting ionizing radiation energy;
circuitry for detecting an emission from the ionizing radiation emission module and for measuring or for determining cumulative emissions of the ionizing radiation emission module and for emitting an emission signal based on the measured or determined cumulative emissions; and
circuitry for preventing excessive cumulative emissions by responding to the emission signal by preventing activation of the ionizing radiation emission module if further activation of the ionizing radiation emission module would permit the user to release more than 30 joules of ionizing radiation energy via the ionizing radiation emission module.

10. The system of claim 2, further comprising:
circuitry for transmitting an image indicating a position of the body part relative to the emission module.

11. The system of claim 2, further comprising:
circuitry for sensing a position of the emission module.

12. The system of claim 2, further comprising:
circuitry for triggering an emission of visible light.

13. The system of claim 2, further comprising:
circuitry for triggering an emission of visible light responsive to the sensor signal.

14. The system of claim 2 in which the emission module comprises:
an ionizing radiation emission module.

15. The system of claim 2 in which the wearable article comprises:
circuitry for receiving one or more therapeutically relevant signals.

16. The system of claim 2, further comprising:
circuitry for sensing a type of the emission module or of the energy.

17. The system of claim 2 in which the circuitry for resetting the emission module comprises:
a network linkage;
a receiver communicably coupled with the circuitry for resetting and with the network linkage; and
the circuitry for resetting the emission module responsive to a remote signal indicative of a sensor signal emitted by the circuitry for emitting and a certification signal output by the circuitry for outputting a certification signal, wherein the remote signal comprises a signal received by the receiver via the network linkage.

18. The system of claim 2 in which the wearable article comprises:
circuitry for transmitting data wirelessly from at least one of the one or more sensing elements.

19. The system of claim 2, further comprising:
at least one of the one or more sensing elements operable for transmitting information associated with a digital image of the body part.

20. The system of claim 2, further comprising:
second circuitry for detecting non-ionizing radiation energy from the body part; and
another article configured to support the second circuitry.

21. The system of claim 2, further comprising:
at least one of the one or more sensing elements, including at least circuitry for detecting at least a portion of the energy emitted by the emission module.

22. The system of claim 2, in which the emission module comprises:
a radio frequency emitter.

23. The system of claim 2, in which the emission module comprises:
an x-ray emitter.

24. The system of claim 23, further comprising:
circuitry for detecting an additional action by the user and for emitting a second sensor signal based on the detection of the additional action by the user;
at least one of the one or more sensing elements operable for transmitting information associated with a first digital image of the body part, including at least second circuitry for detecting at least a part of the energy emitted by the emission module;
third circuitry for triggering an emission of visible light responsive to the second sensor signal;
fourth circuitry for capturing a second digital image in response to the second signal and to a third signal based on another detection of another action by the user;
fifth circuitry for sensing a position of the emission module relative to a position of the one or more sensing elements;
sixth circuitry for obtaining an evaluation, based on the sensed position of the emission module relative to the one or more sensing elements, of whether the emission module is positioned to emit energy toward at least one of the one or more sensing elements for imaging;
seventh circuitry for transmitting a third digital image indicating a position of the body part relative to the emission module;
eighth circuitry for sensing a type of the emission module or of the energy emitted by the emission module;
ninth circuitry for detecting non-ionizing radiation energy from the body part;
another article configured to support at least the ninth circuitry;

a display configured to present video data in a vicinity of the emission module; and a speaker configured to present audio data in the vicinity of the emission module.

25. The system of claim 2, in which the emission module comprises:

an ionizing radiation emitter;

circuitry for detecting an emission from and counting cumulative emissions from the ionizing radiation emitter and for outputting an emissions signal based on the emissions; and circuitry for responding to the emission signal by preventing the user from being able to release more than 100 kilojoules of ionizing radiation energy via the ionizing radiation emitter.

26. The system of claim 2, further comprising:

circuitry for detecting an additional action by the user and for emitting a second sensor signal based on a detection of the additional action by the user; and circuitry for capturing a digital image in response to the second sensor signal.

27. The system of claim 2 in which the emission module comprises:

one or more emitters configured for scanning, wherein at least one of the one or more sensing elements is configured to detect output from at least one of the one or more emitters; and circuitry for computing an image resulting from data from the at least one of the one or more sensing elements.

28. The system of claim 2, further comprising:

at least one of the one or more sensing elements, including at least circuitry for detecting at least a portion of the energy emitted by the emission module and circuitry for capturing a first digital image;

circuitry for transmitting a first digital image indicating a position of the body part relative to the emission module;

circuitry for detecting another action by the user and for emitting a second sensor signal based on a detection of the other action by the user; and circuitry for capturing a second digital image in response to the second sensor signal.

29. The system of claim 28, further comprising:

a display configured to present a facial image in a vicinity of the emission module; and a speaker configured to present audio data in the vicinity of the emission module.

30. The system of claim 2, comprising:

the at least one of the one or more sensing elements, including at least circuitry for detecting at least part of the energy emitted by the emission module and for capturing a first digital image that is based on the detected energy and that indicates a position of a body part relative to the emission module;

circuitry for transmitting the first digital image;

circuitry for capturing a second digital image at least in response to a second sensor signal based on another detection of another action by the user;

circuitry for receiving input from a human being; and circuitry for signaling, responsive to received input from the circuitry for receiving input from a human being, whether one or more physiological features in the second digital image are recognizable to a human being.

31. The system of claim 2, further comprising:

circuitry for detecting non-ionizing radiation energy from the body part;

circuitry for capturing a digital image at least in response to a second sensor signal based on a detection of an additional action by the user;

circuitry for receiving input from a human being;

circuitry for signaling, responsive to received input from the circuitry for receiving input from a human being, whether one or more physiological features in the digital image are recognizable to a human being; and another article configured to support the circuitry for detecting non-ionizing radiation energy.

32. The system of claim 31, further comprising:

circuitry for detecting a further additional action by the user and for emitting a third sensor signal responsive to detection of the further additional action by the user; and circuitry for triggering an emission of visible light responsive to the third sensor signal.

33. The system of claim 31, further comprising:

circuitry for sensing a position of the emission module; and circuitry for sensing a type of the emission module or of the energy.

34. The system of claim 2, further comprising:

circuitry for detecting an additional action by the user and for emitting a second sensor signal based on the detected additional action by the user;

an interface configured to present data in response to a third sensor signal based on another detection of another action by the user;

a common structure supporting the emission module and the interface;

at least one of the one or more sensing elements operable for transmitting information associated with a first digital image of the body part; and a speaker configured to present audio data in a vicinity of the emission module.

35. The system of claim 2, further comprising:

circuitry for detecting another action by the user and for emitting a second sensor signal based on the detection of the other action by the user;

circuitry for capturing a digital image of the body part in response to the second sensor signal;

at least one of the one or more sensing elements operable for transmitting information associated with the digital image of the body part;

an interface configured to present data in response to a third sensor signal based on a third detection of a third action by the user; and a common structure supporting the emission module and the interface.

36. The system of claim 35, further comprising:

a display configured to present video data in a vicinity of the emission module.

37. The system of claim 2:

wherein the circuitry for certifying the user is configured to authenticate an identity of the user by performing at least one of voice, fingerprint, password, cryptographic or biometric authentication; and wherein the circuitry for certifying the user is configured to determine that the user is qualified to use the emission module by performing a skills verification.

38. A system comprising:

an emission module operable for emitting energy through a wireless medium;

circuitry for detecting an action by a user;

circuitry for emitting a sensor signal responsive to detected action by the user;

circuitry for receiving user input;

circuitry for certifying the user at least partly responsive to received user input, wherein the circuitry for certifying is configured to certify the user by at least one of authenticating an identity of the user or verifying that the user is qualified to use the emission module;

circuitry for outputting a certification signal based on the user certification;

circuitry for resetting the emission module partly based on the sensor signal and partly based on the certification signal;

one or more sensing elements for receiving a portion of the energy through a body part from the emission module;

a wearable article configured to support the one or more sensing elements to receive the portion of the energy through the body part from the emission module;

circuitry for detecting an additional action by the user and for emitting a second sensor signal based on the detected additional action by the user;

circuitry for capturing a digital image responsive to the second sensor signal; and circuitry for receiving a signal indicating a failure to recognize one or more physiological features in the digital image and for providing user guidance in response to the signal indicating the failure to recognize one or more physiological features in the digital image.

39. A system comprising:

an emission module operable for emitting energy through a wireless medium;

circuitry for detecting an action by a user;

circuitry for emitting a sensor signal responsive to detected action by the user;

circuitry for receiving user input;

circuitry for certifying the user at least partly responsive to received user input, wherein the circuitry for certifying is configured to certify the user by at least one of authenticating an identity of the user or verifying that the user is qualified to use the emission module;

circuitry for outputting a certification signal responsive to the user certification;

circuitry for resetting the emission module partly based on the sensor signal and partly based on the certification signal;

one or more sensing elements for receiving a portion of the energy through a body part from the emission module;

a wearable article configured to support the one or more sensing elements to receive the portion of the energy through the body part from the emission module;

circuitry for detecting an additional action by the user and for emitting a second sensor signal based on the detected additional action by the user;

circuitry for capturing a digital image at least in response to the second sensor signal;

circuitry for receiving a signal indicating a failure to recognize one or more physiological features in the digital image and for providing user guidance in response to the signal indicating the failure to recognize one or more physiological features in the digital image; and circuitry for detecting non-ionizing radiation energy from the body part.

40. The system of claim 39, further comprising:

a interface configured to present data in response to a third sensor signal based on another detection of another action by the user.

41. The system of claim 39, further comprising:

a display configured to present a facial image in a vicinity of the emission module; and a speaker configured to present audio data in a vicinity of the emission module.

42. A system comprising:

an emission module operable for emitting energy through a wireless medium;

circuitry for detecting an action by a user;

circuitry for emitting a sensor signal responsive to the detected action by the user;

circuitry for receiving user input;

circuitry for certifying the user at least partly responsive to the received user input, wherein the circuitry for certifying the user is configured to certify the user by at least one of authenticating an identity of the user or verifying that the user is qualified to use the emission module;

circuitry for outputting a certification signal based on the user certification;

circuitry for resetting the emission module partly based on the sensor signal and partly based on the certification signal;

one or more sensing elements for receiving a portion of the energy through a body part from the emission module;

a wearable article configured to support the one or more sensing elements to receive the portion of the energy through the body part from the emission module;

circuitry for detecting a second action by the user and for emitting a second sensor signal based on the detected second action by the user;

a common structure supporting the emission module and the interface;

at least one of the one or more sensing elements operable for transmitting information associated with a first digital image of the body part;

a speaker configured to present audio data in a vicinity of the emission module;

circuitry for capturing a second digital image at least in response to the second sensor signal;

circuitry for receiving a signal indicating a failure to recognize one or more physiological features in the second digital image and for providing user guidance in response to the signal indicating the failure to recognize one or more physiological features in the second digital image; and a display configured to present a facial image in a vicinity of the emission module.

43. A system comprising:

an emission module operable to wirelessly transmit energy through a body part;

at least one sensing element configured to receive a portion of the energy transmitted through the body part by the emission module;

a certification module configured to receive user input to certify a user at least partly responsive to received user input and to emit a certification signal based on the user certification, wherein the certification module is configured to certify the user by at least one of authenticating an identity of the user or verifying that the user is qualified to use the emission module;

at least one sensor configured to detect an action by a user and to provide a sensor signal based on the action by the user;

circuitry for resetting the emission module partly based on the certification signal from the certification module and partly based on the provided sensor signal; and a wearable article configured to support and position the at least one sensing element to receive the portion of the energy transmitted through the body part by the emission module the wearable article being an article of clothing.

* * * * *